US010111914B2

(12) United States Patent
Bailey et al.

(10) Patent No.: US 10,111,914 B2
(45) Date of Patent: Oct. 30, 2018

(54) COMPOSITIONS AND METHODS COMPRISING BACTERIA FOR IMPROVING BEHAVIOR IN NEURODEVELOPMENTAL DISORDERS

(71) Applicant: California Institute of Technology, Pasadena, CA (US)

(72) Inventors: Antoinette Bailey, Pasadena, CA (US); Sarkis K. Mazmanian, Porter Ranch, CA (US); Paul H. Patterson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/925,510

(22) Filed: Oct. 28, 2015

(65) Prior Publication Data

US 2016/0120917 A1 May 5, 2016

Related U.S. Application Data

(60) Provisional application No. 62/072,905, filed on Oct. 30, 2014.

(51) Int. Cl.
*A61K 35/741* (2015.01)
*A61K 35/74* (2015.01)

(52) U.S. Cl.
CPC .......... *A61K 35/741* (2013.01); *A61K 35/74* (2013.01)

(58) Field of Classification Search
None
See application file for complete search history.

(56) References Cited

U.S. PATENT DOCUMENTS

| | | |
|---|---|---|
| 5,443,826 A | 8/1995 | Brody |
| 5,951,977 A | 9/1999 | Nisbet et al. |
| 7,041,814 B1 | 5/2006 | Weinstock et al. |
| 7,731,976 B2 | 6/2010 | Cobb et al. |
| 7,749,509 B2 | 7/2010 | Cobb et al. |
| 8,192,733 B2 | 6/2012 | Cobb et al. |
| 9,452,189 B2 | 9/2016 | Mazmanian et al. |
| 2002/0013270 A1 | 1/2002 | Bolte |
| 2004/0005304 A1 | 1/2004 | Brudnak |
| 2004/0028689 A1 | 2/2004 | Borody |
| 2004/0170617 A1 | 9/2004 | Finegold |
| 2006/0167057 A1 | 7/2006 | Kong et al. |
| 2006/0177424 A1 | 8/2006 | Cobb et al. |
| 2010/0303782 A1 | 12/2010 | Cobb et al. |
| 2011/0081320 A1 | 4/2011 | Westall et al. |
| 2011/0118135 A1 | 5/2011 | State et al. |
| 2012/0087895 A1* | 4/2012 | Mazmanian ......... A61K 35/741 424/93.4 |
| 2012/0252775 A1 | 4/2012 | Finegold |
| 2012/0190055 A1 | 7/2012 | Cezar et al. |
| 2012/0207726 A1 | 8/2012 | Lipkin et al. |
| 2012/0237482 A1 | 9/2012 | Rodriguez |
| 2013/0115257 A1 | 5/2013 | Gysemans et al. |
| 2014/0065132 A1 | 6/2014 | Hsaio et al. |
| 2015/0050246 A1 | 2/2015 | Jones et al. |
| 2016/0120917 A1 | 5/2016 | Bailey et al. |
| 2016/0120920 A1 | 5/2016 | Hsiao et al. |
| 2016/0193256 A1 | 7/2016 | Honda et al. |
| 2016/0339065 A1 | 11/2016 | Adams et al. |

FOREIGN PATENT DOCUMENTS

| | | |
|---|---|---|
| EP | 2 624 863 B1 | 4/2016 |
| EP | 3072524 | 9/2016 |
| JP | 2008-532033 | 8/2008 |
| WO | WO 9611014 | 4/1996 |
| WO | WO 02/07741 | 1/2002 |
| WO | WO 2006/090185 A1 | 8/2006 |
| WO | WO 2006/110406 | 10/2006 |
| WO | WO 2009/055362 | 4/2008 |
| WO | WO2010/056985 A2 | 5/2010 |
| WO | WO 2010/111516 A2 | 9/2010 |
| WO | WO2011139914 | 11/2011 |
| WO | WO 2012/048152 A2 | 12/2012 |
| WO | WO 2014/121301 | 8/2014 |
| WO | WO2015/181449 A1 | 12/2015 |
| WO | WO2016/069792 | 5/2016 |
| WO | WO2016/069801 | 5/2016 |
| WO | WO 2016/110768 A1 | 7/2016 |

(Continued)

OTHER PUBLICATIONS

Robinson et al., Microbiology and Molecular Biology Reviews, 2010, vol. 74, No. 3 p. 453-476.*
Kang et al., PLOS ONE, Jul. 2013, vol. 8, issue 7, e68322, p. 1-14, and Supplemental contents 30 pages.*
Extended European Search Report dated Jun. 24, 2016, issued in EP Patent Application No. 16164727.6.
Notice of Allowance dated Jul. 6, 2016 in U.S. Appl. No. 13/267,748.
Partial Supplementary European Search Report dated May 2, 2016 issued in EP Patent Application No. 13832132.8.
Petra, Louis, "Does the human gut mircrobiota contribute to the etiology of autism spectrum disorders?", Digestive diseases and sciences, vol. 57, No. 8, Jun. 27, 2012, pp. 1987-1989.
Collins et al., The Interplay Between the Intestinal Microbiota and the Brain. Nature Reviews—Microbiology. 2012, vol. 10(11), p. 735-742.

(Continued)

*Primary Examiner* — Kade Ariani
(74) *Attorney, Agent, or Firm* — Knobbe, Martens, Olson & Bear, LLP

(57) ABSTRACT

Some embodiments include bacterial species for use in treatment of one or more autism spectrum disorder (ASD), and/or schizophrenia symptoms in a subject in need thereof. The subject in need thereof can have a gut microbiota signature characteristic of an adult. The bacterial species can include *Bacteroides* (e.g., *B. fragilis, B. thetaiomtaomicron,* and/or *B. vulgatus*), and/or *Enterococcus* (e.g., *E. faecalis, E. faecium, E. hirae, E. avium, E. durans, E. gallinarum,* or *E. casseliflavus*). Upon treatment, one or more ASD-related behaviors can be improved in the subject.

16 Claims, 4 Drawing Sheets

(56) References Cited

FOREIGN PATENT DOCUMENTS

WO WO 2017/205302 A1 11/2017
WO WO 2017/220708 12/2017

OTHER PUBLICATIONS

Hsaio, Gastrointestinal Issues in Autism Spectrum Disorder. Harvard Review of Psychiatry. Mar.-Apr. 2014 vol. 22(2):104-111.
Hsaio et al., Microbiota Modulate Behavioral and Physiological Abnormalities Associated with Neurodevelopmental Disorders. Cell. 2013. vol. 155(7), p. 1451-1463.
International Search Report and Written Opinion dated Jun. 30, 2016 for international application PCT/US 15/57891.
U.S. Appl. No. 14/925,242, filed Oct. 28, 2015, Hsaio et al.
U.S. Appl. No. 14/925,240, filed Oct. 28, 2015, Hsaio et al.
Adams et al. (2011). Gastrointestinal flora and gastrointestinal status in children with autism—comparisons to typical children and correlation with autism severity. BMC Gastroenterol 11, 22.
Al-Asmakh et al. (2012). Gut microbial communities modulating brain development and function, Gut Microbes 3, 366-373.
Altieri et al. (2011). Urinary p-cresol is elevated in small children with severe autism spectrum disorder. Biomarkers 16, 252-260.
Amaral et al. (2008). Commensal microbiota Is fundamental for the development of inflammatory pain. Proc Natl Acad Sci U S A 105, 2193-2197.
Amasheh et al. (2009). Na+ absorption defends from paracellular back-leakage by claudin-8 upregulation. Biochem Biophys Res Commun 378, 45-50.
Atladottir, et al. (2010). Maternal infection requiring hospitalization during pregnancy and autism spectrum disorders. J Autism Dev Disord 40, 1423-1430.
Bailey, K.R., and Crawley, J.N. (2009). Anxiety-Related Behaviors in Mice. In Methods of Behavior Analysis in Neuroscience, J.J. Buccafusco, ed. (Boca Raton (FL)).
Bercik et al. (2011). The anxiolytic effect of Bifidobacterium longum NCC3001 involves vagal pathways for gut-brain communication. Neurogastroenterol Motil 23, 1132-1139.
Blumberg, R., and Powrie, F. (2012). Microbiota, disease, and back to health: a metastable journey. Sci Transl Med 4, 137rv137.
Boksa, P. (2010). Effects of prenatal infection on brain development and behavior: a review of findings from animal models. Brain Behav Immun 24, 881-897.
Bourin et al. (2007). Animal models of anxiety in mice. Fundamental & clinical pharmacology 21, 567-574.
Bravo et al. (2011). Ingestion of Lactobacillus strain regulates emotional behavior and central GABA receptor expression in a mouse via the vagus nerve. Proc Natl Acad Sci U S A 108, 16050-16055.
Breiman, L. (2001). Random forests. Mach Learn 45, 5-32.
Brown, et al. (2000). Stress produced by gavage administration in the rat. Contemporary topics in laboratory animal science / American Association for Laboratory Animal Science 39, 17-21.
Buie, et al. (2010), Evaluation, diagnosis, and treatment of gastrointestinal disorders in individuals with ASDs: a consensus report. Pediatrics 125 Suppl 1, S1-18.
Bull et al. (2003). Indolyl-3-acryloylglycine (IAG) is a putative diagnostic urinary marker for autism spectrum disorders. Med Sci Monit 9, CR422-425.
Burlingham et al. (2003). 34S isotope effect on sulfate ester hydrolysis: mechanistic implications. J Am Chem Soc 125, 13036-13037.
Campbell et al., Bacterial diversity, community structure and potential growth rates along an estuarine salinity gradient, Isme J, (2012).
Canitano, R., and Scandurra, V. (2008). Risperidone in the treatment of behavioral disorders associated with autism in children and adolescents. Neuropsychiatr Dis Treat 4, 723-730.
Caporaso et al. (2010). PyNAST: a flexible tool for aligning sequences to a template alignment. Bioinformatics 26, 266-267.
Caporaso et al. (2010). QIIME allows analysis of high-throughput community sequencing data. Nat Methods 7, 335-336.

CDC (2012). Prevalence of autism spectrum disorders—autism and developmental disabilities monitoring network, 14 sites, United States, 2008. MMWR Surveill Summ 61, 1-19.
Clemente et al. (2012). The impact of the gut microbiota on human health: an integrative view. Cell 148, 1258-1270.
Cohen-Poradosu et al. (2011). Bacteroides fragilis-stimulated interleukin-10 contains expanding disease. The Journal of infectious diseases 204, 363-371.
Collins et al. (2012). The interplay between the intestinal microbiota and the brain. Nat Rev Microbiol 10, 735-742.
Coury, et al. (2012). Gastrointestinal conditions in children with autism spectrum disorder: developing a research agenda, Pediatrics 130 Suppl 2, S160-168.
Critchfield, et al. (2011). The potential role of probiotics in the management of childhood autism spectrum disorders. Gastroenterology research and practice 2011, 161358.
Cryan, J.F., and Dinan, T.G. (2012). Mind-altering microorganisms: the impact of the gut microbiota on brain and behaviour. Nat Rev Neurosci 13, 701-712.
De Hoon et al. (2004). Open source clustering software. Bioinformatics 20, 1453-1454.
De Magistris et al. (2010). Alterations of the intestinal barrier in patients with autism spectrum disorders and in their first-degree relatives. J Pediatr Gastroenterol Nutr 51, 418-424.
Desbonnet, et al. (2013). Microbiota is essential for social development in the mouse. Molecular psychiatry.
D'Eufemia, et al. (1996). Abnormal intestinal permeability in children with autism. Acta Paediatr 85, 1076-1079.
Edgar, et al. (2011). UCHIME improves sensitivity and speed of chimera detection. Bioinformatics 27, 2194-2200.
Edgar, R.C. (2010). Search and clustering orders of magnitude faster than BLAST. Bioinformatics 26, 2460-2461.
Ewaschuk, et al. (2008). Secreted bioactive factors from Bifidobacterium infantis enhance epithelial cell barrier function. Am J Physiol Gastrointest Liver Physiol 295, G1025-1034.
Extended European Search Report dated Mar. 3, 2014 for European Patent Application No. 11831629.8 filed Oct. 6, 2011.
Faith, D.P. (1992). Conservation Evaluation and Phylogenetic Diversity. Biol Conserv 61, 1-10.
Finegold, et al. (2002). Gastrointestinal microflora studies in late-onset autism. Clin Infect Dis 35, S6-S16.
Finegold, et al. (2010). Pyrosequencing study of fecal microflora of autistic and control children. Anaerobe 16, 444-453.
Finegold, et al. (2012). Microbiology of regressive autism. Anaerobe 18, 260-262.
Finegold, S.M. (2011). Desulfovibrio species are potentially important in regressive autism. Medical hypotheses 77, 270-274.
Frye, et al. (2013). Unique acyl-carnitine profiles are potential biomarkers for acquired mitochondrial disease in autism spectrum disorder. Translational psychiatry 3, e220.
Ganapathy et al., "Endogenous Elevation of Homocysteine Induces Retinal Neuron Death in the Cystathionine-Beta-Synthenase Mutant Mouse," Invest. Opthamol. Vis. Sci., 50(9);4460-4470 (2009).
Geyer, M.A., and Swerdlow, N.R. (2001). Measurement of startle response, prepulse inhibition, and habituation. Curr Protoc Neurosci Chapter 8, Unit 8 7.
Gondalia, et al. (2012). Molecular characterisation of gastrointestinal microbiota of children with autism (with and without gastrointestinal dysfunction) and their neurotypical siblings. Autism Res 5, 419-427.
Gorrindo, et al. (2012), Gastrointestinal dysfunction in autism; parental report, clinical evaluation, and associated factors. Autism Res 5, 101-108.
Gorrindo, et al. (2013). Enrichment of elevated plasma f2t-isoprostane levels in individuals with autism who are stratified by presence of gastrointestinal dysfunction. PLoS One 8, e68444.
Grenham, G. Clarke, J. F. Cryan, T. G. Dinan, Brain-gut-microbe communication in health and disease. Front Physiol 2, 94 (Dec. 7, 2011).
Grimes, A.J. (1959). Synthesis of 35S-labelled arylsulphates by intact animals and by tissue preparations, with particular reference to I-tyrosine O-sulphate. Biochem J 73, 723.

(56) References Cited

OTHER PUBLICATIONS

Grimsley, et al. (2011). Development of social vocalizations in mice. PloS one 6, e17460.
Gulati et al., Mouse Background Strain Profoundly Influences Paneth Cell Function and Intestinal Microbial Composition, PLoS One 7, e32403 (2012).
Hallmayer, et al. (2011). Genetic heritability and shared environmental factors among twin pairs with autism. Arch Gen Psychiatry 68, 1095-1102.
Hammock et al., "2003 Progress Report: Environmental Factors in the Etiology of Autism: Analytic Biomarkers (xenobiotic) Core," Extramural Research, United States Environmental Protection Agency (2003), retrieved online from EPA. <http://cfpub.epa.gov/ncer_abstracts/index.cfm/fuseaction/display.abstractDetail/abstract/7872/report/2003>.
Han, et al. (2012). Autistic-like behaviour in Scn1a+/− mice and rescue by enhanced GABA-mediated neurotransmission. Nature 489, 385-390.
Hansen et al. The colitis-associated transcriptional profile of commensal Bacteroides thetaiotaomicron enhances adaptive immune responses to a bacterial antigen. PLoS One. 2012;7(8):e42645. doi: 10.1371/journal.pone.0042645. Epub Aug. 3, 2012.
Heljtz, et al. (2011). Normal gut microbiota modulates brain development and behavior. Proc Natl Acad Sci U S A 108, 3047-3052.
Hering, et al. (2012). Determinants of colonic barrier function in inflammatory bowel disease and potential therapeutics. The Journal of physiology 590, 1035-1044.
Holmes, et al. (2006). Claudin profiling in the mouse during postnatal intestinal development and along the gastrointestinal tract reveals complex expression patterns. Gene Expr Patterns 6, 581-588.
Hooper, et al. (2012). Interactions between the microbiota and the immune system. Science 336, 1268-1273.
Horvath, K., and Perman, J.A. (2002). Autism and gastrointestinal symptoms. Curr Gastroenterol Rep 4, 251-258.
Hsiao et al., "Microbiota modulate behavioral and physiological abnormalities associated with neurodevelopmental disorders," Cell, vol. 155, No. 7, Dec. 1, 2013.
Hsiao, E.Y., and Patterson, P.H. (2011). Activation of the maternal immune system induces endocrine changes in the placenta via IL-6. Brain Behav Immun 25, 604-615.
Hsiao, et al. (2012). Modeling an autism risk factor in mice leads to permanent immune dysregulation. Proc Natl Acad Sci U S A 109, 12776-12781.
Huang, et al. (2011). The human commensal Bacteroides fragilis binds intestinal mucin. Anaerobe 17, 137-141.
Ibrahim, et al. (2009). Incidence of gastrointestinal symptoms in children with autism: a population-based study. Pediatrics 124, 680-686.
International Search Report and Written Opinion dated Feb. 27, 2012 for International Application PCT/US2011/055159, filed Oct. 6, 2011.
International Search Report and Written Opinion dated Jan. 12, 2016 in International Application No. PCT/US15/57888.
International Search Report and Written Opinion dated Jan. 12, 2016 in International Application No. PCT/US15/57897.
International Search Report dated Feb. 28, 2014 for International Patent Application No. PCT/US2013/057148 filed Aug. 28, 2013.
Kang, et al. (2013). Reduced Incidence of Prevotella and Other Fermenters in Intestinal Microflora of Autistic Children. PLoS One 8, e68322.
Kau, et al. (2011). Human nutrition, the gut microbiome and the immune system. Nature 474, 327-336.
Keszthelyi, et al. (2009). Understanding the role of tryptophan and serotonin metabolism in gastrointestinal function. Neurogastroenterol Motil 21, 1239-1249.
Kidd, Autism, an extreme challenge to integrative medicine. Part 2: medical management. Altern. Med. Rev. vol. 7, No. 6, pp. 472-499 (2002).
Knights, et al. (2011). Supervised classification of human microbiota. FEMS microbiology reviews 35, 343-359.
Koenig, et al. (2011). Succession of microbial consortia in the developing infant gut microbiome. Proc Natl Acad Sci U S A 108 Suppl 1, 4578-4585.
Kohane, et al. (2012). The co-morbidity burden of children and young adults with autism spectrum disorders. PLoS One 7, e33224.
Korosi, et al. (2012). Early-life stress mediated modulation of adult neurogenesis and behavior. Behav Brain Res 227, 400-409.
Kursa, M.B., and Rudnicki, W.R. (2010). Feature Selection with the Boruta Package. J Stat Softw 36, 1-13.
Lafaye, et al. (2004), Profiling of sulfoconjugates in urine by using precursor ion and neutral loss scans in tandem mass spectrometry. Application to the investigation of heavy metal toxicity in rats. J Mass Spectrom 39, 655-664.
Lazic, S.E. (2013). Comment on "Stress in puberty unmasks latent neuropathological consequences of prenatal immune activation in mice". Science 340, 811; discussion 811.
Leatham, et al. (2009). Precolonized human commensal *Escherichia coli* strains serve as a barrier to *E. coli* O157:H7 growth in the streptomycin-treated mouse intestine. Infect Immun 77, 2876-2886.
Lee et al., in International Meeting for Autism Research (Toronto, Canada, May 17-19, 2012).
Lee, A., and Gemmell, E. (1972). Changes in the mouse intestinal microflora during weaning: role of volatile fatty acids. Infect Immun 5, 1-7.
Lozupone, C., and Knight, R. (2005). UniFrac: a new phylogenetic method for comparing microbial communities. Appl Environ Microbiol 71, 8228-8235.
Ludwig, et al. (2004). ARB: a software environment for sequence data. Nucleic Acids Res 32, 1363-1371.
MacFabe, D.F. (2012). Short-chain fatty acid fermentation products of the gut microbiome: implications in autism spectrum disorders. Microbial Ecology in Health & Disease 23, 19260.
Malkova, et al. (2012). Maternal immune activation yields offspring displaying mouse versions of the three core symptoms of autism. Brain Behav Immun 26, 607-616.
Mandal, et al. (2011). Maternal immune stimulation during pregnancy affects adaptive immunity in offspring to promote development of TH17 cells. Brain Behav Immun 25, 863-871.
Matsumoto, et al. (2012). Impact of intestinal microbiota on intestinal luminal metabolome. Sci Rep 2, 233.
Mayer, E.A. (2011). Gut feelings: the emerging biology of gut-brain communication, Nat Rev Neurosci 12, 453-466.
Mazmanian, et al. (2008). A microbial symbiosis factor prevents intestinal inflammatory disease. Nature 453, 620-625.
Mazurek, et al. (2013). Anxiety, sensory over-responsivity, and gastrointestinal problems in children with autism spectrum disorders. J Abnorm Child Psychol 41, 165-176.
Ming, et al. (2012). Metabolic perturbance in autism spectrum disorders: a metabolomics study. Journal of proteome research 11, 5856-5862.
Mulder, et al. (2004). Platelet serotonin levels in pervasive developmental disorders and mental retardation: diagnostic group differences, within-group distribution, and behavioral correlates. J Am Acad Child Adolesc Psychiatry 43, 491-499.
Nicholson, et al. (2012). Host-gut microbiota metabolic interactions. Science 336, 1262-1267.
Nikolov, et al. (2009). Gastrointestinal symptoms in a sample of children with pervasive developmental disorders. J Autism Dev Disord 39, 405-413.
Novarino, et al. (2012). Mutations in BCKD-kinase lead to a potentially treatable form of autism with epilepsy. Science 338, 394-397.
Ochoa-Reparaz, et al. (2010). Central nervous system demyelinating disease protection by the human commensal Bacteroides fragilis depends on polysaccharide A expression. J Immunol 185, 4101-4108.
Odamaki, et al. (2008). Distribution of different species of the Bacteroides fragilis group in individuals with Japanese cedar pollinosis. Appl Environ Microbiol 74, 6814-6817.
Office Action dated Apr. 1, 2015 for European Patent Application No. 11831 629.8-1456 filed on Oct. 6, 2011.

(56) References Cited

OTHER PUBLICATIONS

Office Action dated Aug. 18, 2015 for Japanese Patent Application No. 2013-532955 filed Oct. 6, 2011 (with English translation).
Office Action dated Nov. 10, 2014 for European Patent Application No. 11831629.8 filed Oct. 6, 2011.
Office Action dated Nov. 21, 2013 for U.S. Appl. No. 13/267,748, filed Oct. 6, 2011.
O'Mahony, et al. (2009). Early life stress alters behavior, Immunity, and microbiota in rats: implications for irritable bowel syndrome and psychiatric illnesses. Biological psychiatry 65, 263-267.
Onore, et al. (2012). The role of immune dysfunction in the pathophysiology of autism. Brain Behav Immun 26, 383-392.
Parracho, et al. (2005b). Differences between the gut microflora of children with autistic spectrum disorders and that of healthy children. Journal of medical microbiology 54, 987-991.
Patterson, Maternal Infection and Immune Involvement in Autism, Trends Mol Med 17, 389 (Jul. 2011).
Patterson, P. H. 2011. Modeling features of autism in animals. Pediatric Res 69:34R-40R.
Penagarikano et al., "Absence of CNTNAP2 Leads to Epilepsy, Neuronal Migration Abnormalities, and Core Autism-Related Deficits," Sep. 30, 2011, Cell, vol. 147, p. 235-246.
Perry, et al. (2007). Sensorimotor gating deficits in adults with autism. Biological psychiatry 61, 482-486.
Persico, A.M., and Napolionl, V. (2013). Urinary p-cresol in autism spectrum disorder. Neurotoxicology and teratology 36, 82-90.
Portfors, C.V. (2007). Types and functions of ultrasonic vocalizations in laboratory rats and mice. J Am Assoc Lab Anim Sci 46, 28-34.
Price, et al. (2009). FastTree: Computing Large Minimum Evolution Trees with Profiles Instead of a Distance Matrix, Mol Biol Evol 26, 1641-1650.
Pruesse, et al. (2012). SINA: Accurate high-throughput multiple sequence alignment of ribosomal RNA genes. Bioinformatics 28, 1823-1829.
Quast, et al. (2013). The SILVA ribosomal RNA gene database project: improved data processing and web-based tools. Nucleic Acids Res 41, D590-D596.
Rao, et al. (2009). A randomized, double-blind, placebo-controlled pilot study of a probiotic in emotional symptoms of chronic fatigue syndrome. Gut Pathog 1, 6.
Resta-Lenert, S.C., and Barrett, K.E. (2009). Modulation of intestinal barrier properties by probiotics: role in reversing colitis. Ann N Y Acad Sci 1165, 175-182.
Riehle, et al. (2012). The Genboree Microbiome Toolset and the analysis of 16S rRNA microbial sequences. Bmc Bioinformatics 13.
Rong et al., "Cystathionine Beta Synthase Participates in Murine Oocyte Maturation Mediated by Homocysteine," Reprod. Toxicol., 24(1):89-96 (2007).
Rossignol, D.A., and Frye, R.E. (2012). Mitochondrial dysfunction in autism spectrum disorders: a systematic review and meta-analysis. Mol Psychiatry 17, 290-314.
Round et al.: "Coordination of tolerogenic immune responses by the commensal microbiota." J. Autoimmun., 34:J220-225 (2010).
Round, J.L., and Mazmanian, S.K. (2009). The gut microbiota shapes intestinal immune responses during health and disease. Nat Rev Immunol 9, 313-323.
Round, J.L., and Mazmanian, S.K. (2010). Inducible Foxp3+ regulatory T-cell development by a commensal bacterium of the intestinal microbiota. Proc Natl Acad Sci U S A 107, 12204-12209.
Saldanha, A.J. (2004). Java Treeview-extensible visualization of microarray data. Bioinformatics 20, 3246-3248.
Sandler, et al. (2000). Short-term benefit from oral vancomycin treatment of regressive-onset autism. J Child Neurol 15, 429-435.
Sankoorikal, et al. (2006). A mouse model system for genetic analysis of sociability: C57BL/6J versus BALB/cJ inbred mouse strains. Biological psychiatry 59, 415-423.
Scattoni, et al. (2011). Unusual repertoire of vocalizations in adult BTBR T+tf/J mice during three types of social encounters. Genes, brain, and behavior 10, 44-56.

Schmeisser, et al. (2012). Autistic-like behaviours and hyperactivity in mice lacking ProSAP1/Shank2. Nature 486, 256-260.
Schwartzer, et al. (2013). Maternal immune activation and strain specific interactions in the development of autism-like behaviors in mice. Translational psychiatry 3, e240.
Segata, et al. (2011). Metagenomic biomarker discovery and explanation. Genome biology 12, R60.
Sharma, et al. (2010). Molecular modulation of intestinal epithelial barrier: contribution of microbiota. Journal of biomedicine & biotechnology 2010, 305879.
Shi, et al. (2009). Activation of the maternal immune system alters cerebellar development in the offspring. Brain Behav Immun 23, 116-123.
Silverman, et al. (2010). Behavioural phenotyping assays for mouse models of autism. Nature Reviews Neuroscience 11, 490-502.
Smith et al., Host Genetics and Environmental Factors Regulate Ecological Succession of the Mouse Colon Tissue-Associated Microbiota, PLoS One 7, e30273 (Jan. 2012).
Smith, E.A., and Macfarlane, G.T. (1997). Formation of Phenolic and Indolic Compounds by Anaerobic Bacteria in the Human Large Intestine. Microb Ecol 33, 180-188.
Smith, et al. (2007). Maternal immune activation alters fetal brain development through interleukin-6. J Neurosci 27, 10695-10702.
Sommese, et al. (2012). Evidence of Bacteroides fragilis protection from Bartonella henselae-induced damage. PLoS One 7, e49653.
Song, et al. (2004). Real-time PCR quantitation of clostridia in feces of autistic children. Appl Environ Microbiol 70, 6459-6465.
Suzuki, et al. (2011). Interleukin-6 (IL-6) regulates claudin-2 expression and tight junction permeability in intestinal epithelium. J Biol Chem 286, 31263-31271.
Tabuchi, et al. (2007). A neuroligin-3 mutation implicated in autism increases inhibitory synaptic transmission in mice. Science 318, 71-76.
Tamura, et al. (2011). Loss of claudin-15, but not claudin-2, causes Na+ deficiency and glucose malabsorption in mouse small intestine. Gastroenterology 140, 913-923.
Thomas, et al. (2009). Marble burying reflects a repetitive and perseverative behavior more than novelty-induced anxiety. Psychopharmacology 204, 361-373.
Tillisch, et al. (2013). Consumption of fermented milk product with probiotic modulates brain activity. Gastroenterology 144, 1394-1401 e1394.
Tsai, et al. (2012). Autistic-like behaviour and cerebellar dysfunction in Purkinje cell Tsc1 mutant mice. Nature 488, 647-651.
Turner, J.R. (2009). Intestinal mucosal barrier function in health and disease. Nat Rev Immunol 9, 799-809.
Wang et al., "Is Urinary Indolyl-3-Acryloylglycine a Biomarker for Autism with Gastrointestinal Symptoms?" Biomarkers, 14(8):596-603 (2009).
Wang, et al. (2011). The prevalence of gastrointestinal problems in children across the United States with autism spectrum disorders from families with multiple affected members. Journal of developmental and behavioral pediatrics : JDBP 32, 351-360.
Wang, et al. (2012). Elevated fecal short chain fatty acid and ammonia concentrations in children with autism spectrum disorder. Dig Dis Sci 57, 2096-2102.
White, et al. (2009). Statistical Methods for Detecting Differentially Abundant Features in Clinical Metagenomic Samples, Plos Comput Biol 5.
White, J.F, (2003). Intestinal pathophysiology in autism. Exp Biol Med (Maywood) 228, 639-649.
Wikoff, et al. (2009). Metabolomics analysis reveals large effects of gut microflora on mammalian blood metabolites. Proc Natl Acad Sci U S A 106, 3698-3703.
Williams, et al. (2011). Impaired carbohydrate digestion and transport and mucosal dysbiosis in the intestines of children with autism and gastrointestinal disturbances. PLoS One 6, e24585.
Williams, et al. (2012). Application of novel PCR-based methods for detection, quantitation, and phylogenetic characterization of *Sutterella* species in intestinal biopsy samples from children with autism and gastrointestinal disturbances. MBio 3.
Wirtz, et al. (2007). Chemically induced mouse models of intestinal Inflammation. Nature protocols 2, 541-546.

(56) References Cited

OTHER PUBLICATIONS

Wittebolle, et al. (2009). Initial community evenness favours functionality under selective stress. Nature 458, 623-626.
Won, et al. (2012). Autistic-like social behaviour in Shank2-mutant mice improved by restoring NMDA receptor function. Nature 486, 261-265.
Yang, et al. (2011). Automated three-chambered social approach task for mice. Curr Protoc Neurosci Chapter 8, Unit 8 26.
Yap, et al. (2010). Urinary metabolic phenotyping differentiates children with autism from their unaffected siblings and age-matched controls. Journal of proteome research 9, 2996-3004.
Barbara, et al. (2005) "Interactions between commensal bacteria and gut sensorimotor function in health and disease" The American journal of gastroenterology 100, 2560-2568.
Extended European Search Report dated Jun. 24, 2016, issued in EP16164727.6.
Nieswandt, et al. (2004) "Flow-cytometric analysis of mouse platelet function" Methods Mol Biol 272, 255-268.
Notice of Allowance dated Jul. 6, 2016 in U.S. Appl. No. 13/267,748, filed Oct. 6, 2011.
Office Action dated Nov. 18, 2015 in U.S. Appl. No. 13/267,748, filed Oct. 6, 2011.
Partial Supplementary European Search Report dated May 2, 2016 issued in EP 13832132.8.
Office Action dated Oct. 5, 2016 in U.S. Appl. No. 14/839,041, filed Aug. 28, 2015.
Yadav, et al., "Pharmacological inhibition of gut-derived serotonin synthesis is a potential bone anabolic treatment for osteoporosis", Nature Medicine 16(3):308-312, 2010.
Nemeroff et al., "Are platelets the link between depression and ischemic heart disease?", American Heat Journal 140(4): S57-S62, 2000.
American Psychiatric Association, Diagnostic and Statistical Manual of Mental Disorders (DSM) (5th ed.), Table of Contents, 2013, American Psychiatric Association Publishing, Washington DC, in 9 pages.
Chi, "Clinical, animal studies probe DISC1's role in autism" Spectrum, Mar. 1, 2010, https://spectrumnews.org/news/clinical-animal-studies-probe-disc1s-role-in-autism/.
Kilpinen, et al., Association of DISC1 with autism and Asperger syndrome Molecular Psychiatry (2008) 13, 187-196.
Penagariko et al., "What does CNTNAP2 reveal about autism spectrum disorder?" Trends in Molecular Medicine, 2012, vol. 18, pp. 156-163.
Office Action dated Oct. 7, 2016 in U.S. Appl. No. 14/925,240, filed Oct. 28, 2015.
Extended European Search Report dated Aug. 25, 2016, issued in EP13832132.8.
Office Action dated Mar. 29, 2017 in U.S. Appl. No. 14/012,869.
American Psychiatric Association: Diagnostic and Statistical Manual of Mental Disorders, Fourth Edition, Text Revision. Washington, DC, pp. 69-84, American Psychiatric Association, 2000.
Seltzer, et al., "The Symptoms of Autism Spectrum Disorders in Adolescence and Adulthood" Journal of Autism and Developmental Disorders, vol. 33, No. 6, pp. 565-581, Dec. 2003.
Maslowski, et al., "Diet, gut microbiota and immune responses" Nature Immunology vol. 12 No. 1, pp. 5-9, Jan. 2011.
Office Action dated Feb. 7, 2017 for Japanese Patent Application No. 2016-088694 filed Apr. 27, 2016.
Office Action dated Jun. 13, 2017 in Japanese Application No. 2015-530008.
Office Action dated Mar. 29, 2017 in U.S. Appl. No. 14/012,769.
International Preliminary Report on Patentability dated May 2, 2017 issued in PCT/US2015/057897.
International Preliminary Report on Patentability dated May 2, 2017 issued in PCT/US2015/057888.
International Preliminary Report on Patentability dated May 2, 2017 issued in PCT/US2015/057891.
Office Action dated May 5, 2017 issued in U.S. Appl. No. 14/925,240.
Winek et al., "The Gut Microbiome as Therapeutic Target I Central Nervous System Diseases: Implications for Stroke", Neurotherapeutics 13(4): 762-774, 2016.
Gupta, "The phylogeny of proteobacteria: relationships to other eubacterial phyla and eukaryotes.", FEMS Microbiology Reviews 24 (4):367-402, 2000.
Jandhyala et al., "Role of the normal gut microbiota", World Journal of Gastroenterology 21(9): 8787-8803, 2015.
Lopetuso et al., "Commensal Clostridia: leading players in the maintenance of gut homeostasis", Gut Pathogents 5(1): 23, 2013.
Office Action dated May 25, 2017 in U.S. Appl. No. 14/839,041.
Office Action dated Jul. 20, 2017 in Canadian Application No. 2,813,606, filed Oct. 6, 2011.
Dutta et al., "Men and mice: Relating their ages", Life Sciences, LFS-14535; http://dx.doi.org/10.1016/j.lfs.2015.10.025, 5 pages, 2015.
Calculate mouse age in human years (equivalence), "Mouse age calculator", http://www.age-converter.com/mouse-age-calculator.html, 2 pages, Copyright 2015. Downloaded May 22, 2018. This item refers to a webpage and may have been available in some form at an earlier point in time.
Office Action dated Jan. 11, 2018 in European Application No. 13832132.8, filed Feb. 17, 2015.
Final Office Action dated Jan. 24, 2018 in U.S. Appl. No. 14/925,240.
International Search Report dated Jan. 30, 2018 issued in PCT/US17/63108 filed Nov. 22, 2017.
Ono et al., "Antioxidant compounds have potent anti-fibrillogenic and fibril-destabilizing effects for αsynuclein fibrils in vitro", Journal of Neurochemistry, 2006, 97, 105-115.
Office Action dated Nov. 30, 2017 in U.S. Appl. No. 14/925,242.
Office Action dated Dec. 11, 2017 in U.S. Appl. No. 14/012,769.
Advisory Action dated Apr. 20, 2018 in U.S. Appl. No. 14/012,769.
Office Action dated Apr. 24, 2018 in the U.S. Appl. No. 15/249,870, filed Aug. 29, 2016.
International Search Report and Written Opinion dated May 14 ,2018 in PCT App. No. PCT/US2018/017116.
Strati et al., "Altered gut microbiota in Rett syndrome," Microbiome 4: 1-15, Jul. 30, 2016.
Yasui et al. "15q11.2-13.3 chromatin analysis reveals epigenetic regulation of CHRNA7 with deficiencies in Rett and autism brain," Human Molecular Genetics 20: 4311-4323, Aug. 12, 2011.
De Theije. "Neuroimmunomodulation of the Young Brain: Nutrtion, A Gut Feeling," The Netherlands: Utrecht University, 2014, pp. 1-78, retrieved from the internet at https://dspace.library.uu.nl/bitstream/handle/1874/294744/theije%202014.pdf?sequence=2*isAllowed=y. This document bears a retrieval date of Mar. 21, 2018, but may have been available on the internet in some form at an earlier point in time.
FAI Pre-Interview Communication issued on Jun. 11, 2018 in the U.S. Appl. No. 15/893,456, filed Aug. 29, 2016.
Borghi et al., Rett Syndrome: A Focus on Gut Microbiota, International Journal of Molecular Sciences, vol. 18, No. 2, pp. 1-17, dated Feb. 7, 2017.
Chen et al., "Exposure to the Functional Bacterial Amyloid Protein Curli Enhances Alpha-Synuclein Aggregation in Aged Fischer 344 Rats and Caenorhabditis elegans", Scientific Reports, vol. 6, pp. 1-10, 2016.
Farlow et al., "Parkinson Disease Overview", PubMed NCBI, https://www.ncbi.nlm.nih.gov/pubmed/20301402, GeneReviews, abstract pp. 1-2, May 25, 2004, printed May 14, 2018, and listing copyright dates of 1993-1998. The noted reference refers to a web page, and may have been available online in some form at an earlier point in time.
Hung et al., "The Bacterial Amyloid Curli Is Associated with Urinary Source Bloodstream Infection", PLOS One, vol. 9, No. 1, pp. 1-6, Jan. 2014.
Lavatelli et al., "Proteomic typing of amyloid deposits in systematic amyloidoses", Amyloid, vol. 18, No. 4, pp. 177-182, 2011.
Office Action dated May 8, 2018 in Japanese Application No. 2015-530008.
Extended European Search Report dated May 14, 2018 in Application No. 15856096.1.
Office Action dated Aug. 10, 2018 in U.S. Appl. No. 14/925,240.
Office Action dated Jun. 21, 2018 in U.S. Appl. No. 14/012,769.

(56) References Cited

OTHER PUBLICATIONS

Office Action dated Aug. 22, 2018 in Eurasian Application No. 201790811 with English Translation.
Sender et al.. Revised Estimates for the Number of Human and Bacteria Cells in the Body. PLOS Biology. Aug. 19, 2016. 14(8) e1002533, in 10 pages.
Stephen et al. The Microbial Contribution to Human Faecal Mass. Journal of Medical Microbiology. 1980. 13: pp. 45-56.
Macfarlane et al., Chemotaxonomic Analysis of Bacterial Populations Colonizing the Rectal Mucosa in Patients with Ulcerative Colitis. Clinical Infectious Diseases. 2004. vol. 38, pp. 1690-1699.
Guarner et al. 2003. Gut flora in health and disease. The Lancet, vol. 361, Issue 9356, Feb. 8, 2003, pp. 512-519. PMID 12583961. Accessed Sep. 15, 2007.
Sears, C., A dynamic partnership: Celebrating our gut flora. Anaerobe. vol. 11, Issue 5, Oct. 2005, pp. 247-251.
Steinhoff, U., Who controls the crowd? New findings and old questions about the intestinal microflora. Immunology Letters. vol. 99, Issue 1, Jun. 15, 2005, pp. 12-16.
Gibson Rg. 2004. Fibre and effects on probiotics (the prebiotic concept). Clinical Nutrition Supplements, vol. 1, Issue 2, pp. 25-31.
Beaugerie et al. 2004. Antibiotic-associated diarrhoea. Best Practice & Research Clinical Gastroenterology, vol. 18, Issue 2, pp. 337-352.
Todar, K. The Normal Bacterial Flora of Humans. Accessible on the world wide web at www.textbookofbacteriology.normalflora.html. Todar's Online Textbook of Bacteriology (2012). As this item refers to a web page, it may have been available in some form at an earlier point in time.
Ria Science, "Scientists: Bacteria in the human body are not 10 times larger than their cells", accessible on the world wide web at https://ria.ru/science/20160111/1357907466.html, (with English Translation), updated Jan. 11, 2016, 14 pages. While this item bears an "updated" date of Jan. 11, 2016, as it refers to a web page, it may have been available in some form at an earlier point in time.

\* cited by examiner

COMPOSITIONS AND METHODS COMPRISING BACTERIA FOR IMPROVING BEHAVIOR IN NEURODEVELOPMENTAL DISORDERS

CROSS-REFERENCE TO RELATED APPLICATIONS

The present application claims the benefit of U.S. Provisional Application No. 62/072,905, filed Oct. 30, 2014, which is hereby incorporated by reference in its entirety.

STATEMENT REGARDING FEDERALLY SPONSORED R&D

This invention was made with government support under Grant No. MH100556 awarded by the National Institutes of Health. The government has certain rights in the invention.

BACKGROUND

Background

Autism spectrum disorder (ASD) is a neurodevelopmental disorder that is diagnosed based on presentation with repetitive behaviors and impaired social interaction and communication. The prevalence of ASD in the United States is currently a striking 1 in 68, representing a significant medical and social issue. Although the underlying causes of ASD are largely unknown, both genetic and environmental risk factors are implicated.

Field

Some embodiments described herein relate generally to probiotic compositions, which can be used to treat autism spectrum disorder (ASD) symptoms. In some embodiments, the probiotic compositions can be used to treat ASD symptoms in an individual having an adult microbiotic profile.

SUMMARY

In accordance with some embodiments described herein, a method for improving behavioral performance in a human. The method can comprise identifying a human subject having a gut microbiota signature comprising at least 500 different species of microbes. The method can comprise administering to the human subject an effective amount of one or more *Bacteroides* bacteria. In some embodiments, the method further comprises identifying the gut microbiota signature of the human subject as an adult gut microbiotia signature. In some embodiments, the subject suffers from anxiety, autism spectrum disorder (ASD), schizophrenia, or a pathological condition with one or more of the symptoms of ASD or schizophrenia. In some embodiments, the method further comprises the effective amount of one or more *Bacteroides* bacteria comprises *B. fragilis*. In some embodiments the effective amount of one or more *Bacteroides* bacteria comprises *B. fragilis, B. thetaiotaomicron, B. vulgatus*, or a mixture of two or three of the listed bacteria, for example *B. fragilis* and *B. thetaiotaomicron, B. fragilis* and *B. vulgatus, B. thetaiotaomicron* and *B. vulgatus*, or *B. fragilis, B. thetaiotaomicron*, and *B. vulgatus*. In some embodiments, the method further comprises administering an amount of *Enterococcus* bacteria to the subject. In some embodiments, a sole active ingredient administered to the subject in the method consists essentially of one or more *Bacteroides* bacteria. In some embodiments, a sole active ingredient administered to the subject consists essentially of *B. fragilis*. In some embodiments, the effective amount of one or more *Bacteroides* bacteria is in a composition substantially free of bacteria other than the *Bacteroides* bacteria. In some embodiments, the effective amount of *Bacteroides* bacteria is in a composition substantially free of bacteria other than *B. fragilis*. In some embodiments, the effective amount of one or more *Bacteroidies* bacteria is administered orally. In some embodiments, improving behavioral performance comprises improving a communication behavior, a repetitive behavior, anxiety, or a combination of two or three of these listed behaviors. In some embodiments, the human subject is an adult.

BRIEF DESCRIPTION OF THE DRAWINGS

FIG. 1A depicts entries into the center area. FIG. 1B depicts total distance traveled.

DETAILED DESCRIPTION

Figure 1A:
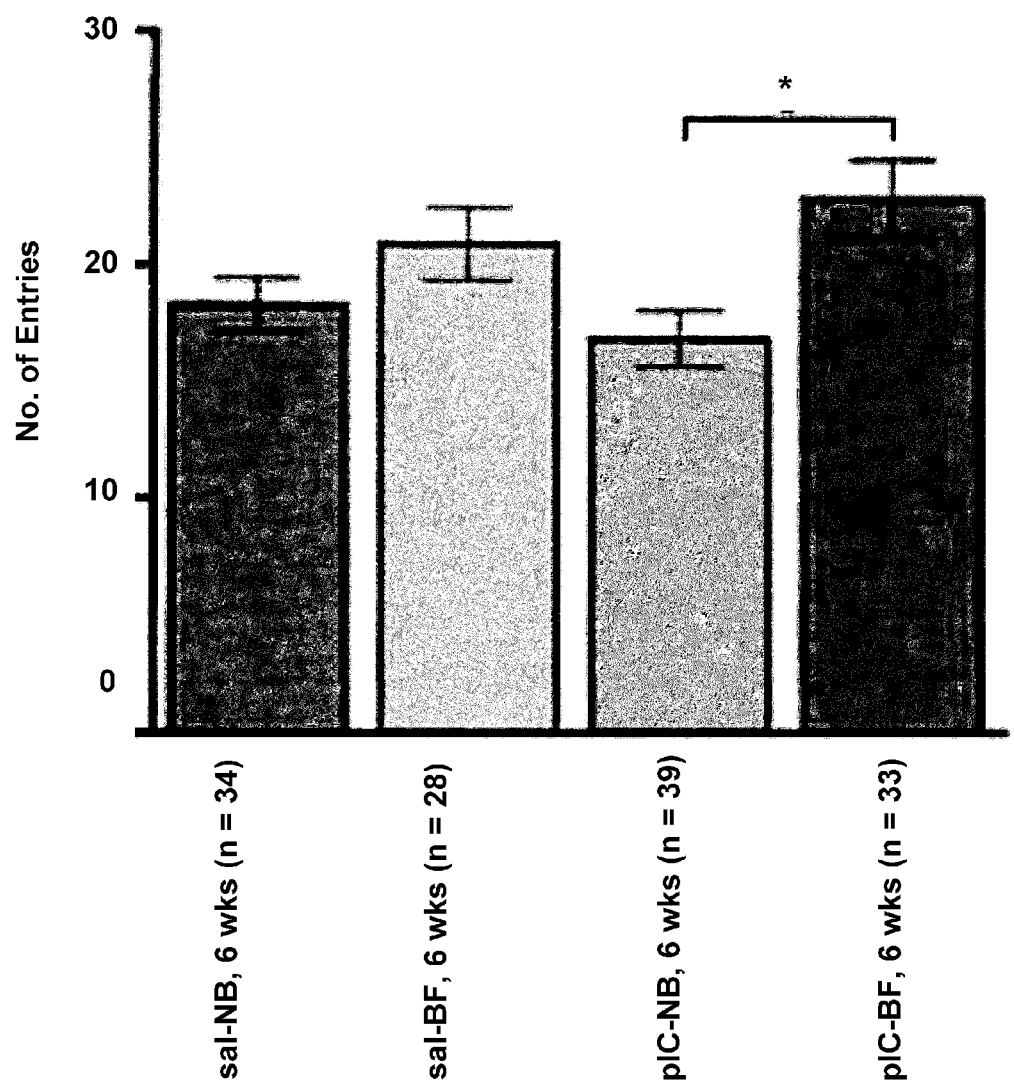
FIG. 1A and FIG. 1B are a series of graphs that treatment of adult maternal immune activation (MIA) mice with a probiotic comprising *B. fragilis* corrects deficits in exploratory behavior in accordance with some embodiments described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Without being limited by any theory, it is contemplated that there can be a gut-immune-brain connection in autism spectrum disorders (ASD). As gut microbiomes can differ in infants and "adults" (three years old or greater), it is contemplated that probiotics do not necessarily have the same effect on an infant gut microbiome as an adult gut microbiome, and thus are not necessarily interchangeable between infants and adults. In accordance with some embodiments described herein, probiotics comprising one or more bacterial species are provided, which can be administered to a subject to treat one or more symptoms of ASD and/or or schizophrenia, and having a gut microbiota signature characteristic of an adult. The ASD and/or schizophrenia symptoms, for example repetitive behavior, anxiety, and deficient communication behavior can be improved following administration of the probiotic, as described herein. In some embodiments, the probiotic comprises one or more of the following bacteria: *Bacteroides fragilis, Bacteroides thetaiotaomicron, Bacteroides vulgatus*, and *Enterococcus faecalis*. The probiotic can improve repetitive behavior, anxiety, and communication behavior in the subject having an adult gut microbiome.

Maternal infection is identified as a primary non-genetic cause of ASD, based on many large epidemiological studies linking maternal bacterial or viral infection during pregnancy increased risk for ASD in the offspring, and on pre-clinical studies in mice, rats and monkeys demonstrating that maternal infection or immune activation during pregnancy yields offspring with behavioral and neuropathological abnormalities relevant to ASD. ASD is also co-morbid with a variety of medical conditions, ranging from seizures to immune dysregulation. Gastrointestinal issues, such as constipation, abdominal pain, intestinal permeability and altered composition of the gut microbiota are prevalent in a significant subset of ASD individuals. Collectively, increasing evidence implicates a potential role for gut-brain interactions in the etiopathogenesis of ASD.

It is noted that, in addition to displaying cardinal behavioral and neuropathological features of ASD and schizophrenia, the maternal immune activation (MIA) mouse model for autism also exhibits ASD-related immunological and gastrointestinal abnormalities. Further, treating MIA offspring at weaning with the human commensal bacterium, *Bacteroides fragilis*, corrects gastrointestinal and behavioral deficits. The gut microbiota is inherited during the birthing process, after which it develops and matures until it reaches an adult microbiota signature based on species composition and abundance. It is contemplated that in accordance with some embodiments described herein, *B. fragilis* provides a potential probiotic treatment for symptoms of ASD and/or schizophrenia.

To examine the ability of *B. fragilis* to correct ASD and schizophrenia behavioral abnormalities during adulthood, adult MIA mouse offspring were treated with *B. fragilis* at 6 weeks of age and then effects on ASD-related behavioral performance were examined. It was observed that treatment of ASD and schizophrenia model offspring with *B. fragilis* (in comparison to untreated controls), corrected anxiety and deficiencies in exploratory behaviors associated with ASD and schizophrenia (see FIG. 1). It was observed that treatment of ASD and schizophrenia model offspring with *B. fragilis* (in comparison to untreated controls) corrected deficiencies in repetitive behaviors associated with ASD and schizophrenia (see FIG. 2). It was also observed that treatment of ASD and schizophrenia model offspring with *B. fragilis* (in comparison to untreated controls), corrected deficiencies in communication behaviors associated with ASD and schizophrenia (see FIG. 3). As such, it is contemplated that in accordance with some embodiments described herein, treatment of a subject having ASD or schizophrenia and having an adult gut microbiota signature can ameliorate the symptoms of ASD and/or schizophrenia. By way of the example, the symptoms can include at least one of: anxiety, repetitive behavior, and deficient communication behavior.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

As used herein, the term "subject" is a vertebrate, such as a mammal. The term "mammal" is defined as an individual belonging to the class Mammalia and includes, without limitation, humans, domestic and farm animals, and zoo, sports, or pet animals, such as sheep, dogs, horses, cats or cows. In some embodiments, the subject is human. In some embodiments, the subject is a non-human primate.

As used herein, the term "condition/disorder/symptom" or "behavioral abnormality" refers to a symptom expressed by a subject including but not limited to anxiety, Fragile X, Rett syndrome, tuberous sclerosis, obsessive compulsive disorder, attention deficit disorder, schizophrenia, autistic disorder (classic autism), Asperger's disorder (Asperger syndrome), pervasive developmental disorder not otherwise specified (PDD-NOS), childhood disintegrative disorder (CDD), or a pathological condition with one or more of the symptoms of ASD.

As used herein, the term "subject in need of the treatment" refers to a subject expressing or suffering from one or more of the behavioral disorder/symptoms mentioned above. In some embodiments, the subject in need of treatment suffers from at least one of schizophrenia, ASD, or a gastrointestinal or immunological pathology associated with ASD or schizophrenia (for example leaky gut syndrome). An appropriately qualified person is able to identify such an individual in need of treatment using standard behavioral testing protocols/guidelines. The same behavioral testing protocols/guidelines can also be used to determine whether there is improvement to the individual's disorder and/or symptoms.

As used herein, the term "improvement in behavioral performance" refers to prevention or reduction in the severity or frequency, to whatever extent, of one or more of the behavioral disorders, symptoms and/or abnormalities expressed by individual suffering from ASD, schizophrenia, or a pathological condition with one or more of the symptoms of ASD or schizophrenia. Non-limiting examples of the behavioral symptoms include impaired communication, impaired sociability, impaired language comprehension and/or production, repetitive behavior, and increased anxiety. The improvement is either observed by the individual taking the treatment themselves or by another person (medical or otherwise). In some embodiments, a probiotic comprising an effective amount of *Bacteroides* and/or *Enterococcus* bacteria as described herein is administered the subject. In some embodiments, sensorimotor gating behavior is improved in the subject after administration of the probiotic. In some embodiments, communication behavior is improved in the subject after administration of the probiotic. As used herein, "communication behavior" refers to communication, language comprehension and production, and sociability, including vocal and non-vocal social communication. In some embodiments, a subject is identified as deficient in communication behavior based on impaired sociability. In some embodiments, a subject is identified as deficient in communication behavior based on impaired language comprehension and/or production.

As used herein, the term "treatment" refers to a clinical intervention made in response to a disease, disorder or physiological condition manifested by a subject, particularly a subject suffering from ASD, schizophrenia, or a pathological condition with one or more of the symptoms of ASD or schizophrenia. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may improve behavioral performance of the subject, including ASD-related behaviors such as sensorimotor gating behavior deficiencies and/or communication behavior deficiencies. As used herein, the term "prevention" refers to any activity that reduces the burden of the individual later expressing those behavioral symptoms. This takes place at primary, secondary and tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications.

"Pharmaceutically acceptable" carriers are ones which are nontoxic to the cell or mammal being exposed thereto at the dosages and concentrations employed. "Pharmaceutically acceptable" carriers in accordance with methods and uses and compositions and kits herein can comprise, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as and nonionic surfactants such as TWEEN™ surfactant, polyethylene glycol (PEG), and PLURONICS™ surfactant. Auxiliary, stabilizer, emulsifier, lubricant, binder, pH adjustor controller, isotonic agent and other conventional additives may also be added to the carriers.

The pharmaceutically acceptable or appropriate carrier in accordance with methods and uses and compositions and kits herein may include other compounds known to be beneficial to an impaired situation of the GI tract, (e.g., antioxidants, such as Vitamin C, Vitamin E, Selenium or Zinc); or a food composition. The food composition can be, but is not limited to, milk, yoghurt, curd, cheese, fermented milks, milk based fermented products, ice-creams, fermented cereal based products, milk based powders, infant formulae, tablets, liquid bacterial suspensions, dried oral supplement, or wet oral supplement.

As used herein, the term "probiotic" refers to live microorganisms, which, when administered in adequate amounts, confer a health benefit on the host. The probiotics in accordance with methods and uses and compositions and kits herein may be available in foods and dietary supplements (for example, but not limited to capsules, tablets, powders, and liquids). Non-limiting examples of foods containing probiotic include dairy products such as yogurt, fermented and unfermented milk, smoothies, butter, cream, hummus, kombucha, salad dressing, miso, tempeh, nutrition bars, and some juices and soy beverages. In some embodiments, the probiotic comprises a single microorganism. In some embodiments, the probiotic comprises a combination of microorganisms. In some embodiments, the probiotic comprises a single composition. In some embodiments, the probiotic comprises two or more compositions, which can be used together, for example administered simultaneously or administered sequentially. It is noted that a probiotic can serve as the "active ingredient" or a composition or compositions for use in administration to a subject. That is, the method, use, and/or composition or compositions (either individually or in the aggregate) can comprise an effective amount of probiotic to improve at least one behavior in a subject. In some embodiments, the probiotic is the sole active ingredient for administration to the subject. In some embodiments, the "sole active ingredient" probiotic for administration to the subject can be provided in a composition or in a method or use that is substantially free of or free of bacteria other than the probiotic, antibiotics, and drugs. Even if the probiotic is the "sole" active ingredient, the composition or composition comprising the probiotic may comprise additional substances (such as buffers, bacterial feedstock, excipients, flavors, and/or food) that do not substantially affect the behavior of the subject, but may be useful for the function of the probiotic or its administration.

In some embodiments, the probiotic is comprised in a composition or compositions that are substantially free of bacteria (other than the probiotic) and/or drugs or antibiotics. By "substantially free" or "substantially absent", it is understood that while a bacteria other than the probiotic, drug, and/or antibiotic may be present in trace amounts, the bacteria other than the probiotic, drug, and/or antibiotic have no appreciable effect on the subject.

As used herein "effective amount" of probiotic refers to a quantity sufficient to achieve a clinically significant change in a behavior of a subject.

As used herein, the term "neutraceutical" refers to a food stuff (as a fortified food or a dietary supplement) that provides health benefits. Nutraceutical foods are not subject to the same testing and regulations as pharmaceutical drugs.

The term "microbiota signature" (or optionally "gut microbiota signature"), including pluralizations and variations of this root term, as used herein refers to a profile of a microbiota in a gut, and can include overall number of microbial organisms in the gut, and/or relative abundance of particular phyla and/or species of microbiota in the gut. An "adult microbiota signature" (or optionally "adult gut microbiota signature"), including pluralizations and variations of this root term, as used herein refers to a microbiota signature characteristic of a human who is at least three years of age. The term "infant microbiota signature" (or optionally "infant gut microbiota signature"), including pluralizations and variations of this root term, as used herein refers to a microbiota signature characteristic of a human under three years of age. As used herein, the term "adult" refers to a human who is at least three years of age.

Without being limited by any theory, a microbiota signature can be affected by environmental factors and life events, for example diet, hygiene, infection or other illness, and developmental events for example hormonal shifts. An infant (under three years old) that is at weaning or immediately post-weaning can be expected to have different microbiome characteristics (and thus a different microbiota signature) than an older individual that has been eating a greater variety of foods, had greater exposure to infection and the like. Accordingly, without being limited by any theory, interventions that affect an individual with an infant microbiota signature (for example probiotic treatments) are not necessarily expected to have comparable or analogous in individuals with an adult microbiota signature, because the infant gut microbiome can differ substantially from the adult microbiome.

A typical newborn gut can have about 100 different species of microbes, while a typical adult (age three years or greater) gut can have about 1000 different species of microbes. In some embodiments an adult gut microbiota signature is characterized by at least about 500 different species of microbes, for example at least about 500, 550, 600, 650, 700, 750, 800, 850, 900, 950, 1000, 1050, 1100, 1150, 1200, 1250, 1300, 1350, 1400, 1450, or 1500 different species, including ranges between any two of the listed values. In some embodiments, an infant gut microbiome has a lower number of total species of microbes than an adult gut microbiome. Optionally, a microbiota signature can also be characterized by relative abundance of various phyla (this metric can be used alone, or in conjunction with total number of different species). In some embodiments, an infant (i.e. under three years of age) gut microbiota signature is characterized by a relative abundance of the following phyla (in order of greatest to least) of Actinobacteria, Proteobacteria, Firmicutes, Bacteroidetes. In some embodiments, an adult gut microbiota signature is characterized by a relative abundance of the following phyla (in order of greatest to least) of: Firmicutes, Bacteroidetes, Actinobacteria, Proteobacteria. In some embodiments, an elderly adult gut microbiota signature is characterized by a relative abundance of the following phyla: Firmicutes, Actinobacteria, Bacteroidetes, Proteobacteria. As such, in some embodiments, an adult gut microbiota signature is characterized by a relative abundance of the following phyla (in order of greatest to least) of: (a) Firmicutes, Bacteroidetes, Actinobacteria, Proteobacteria, or (b) Firmicutes, Actinobacteria, Bacteroidetes, Proteobacteria.

In some embodiments, a gut microbiota signature can be characterized by analysis of the composition of a sample from a subject representative of the gut, for example a fecal sample, or an intestinal biopsy or brush sample. The number of different species in a gut sample and/or the relative makeup of species and/or phyla in a gut sample can be ascertained by identifying nucleic acids characteristic of the different phyla. For example, the sequences of relatively conserved nucleic acids such as the 16s rRNA subunit can be compared. The comparison can be performed by a number of techniques known to one skilled in the art, for example, nucleic acid analysis such microarray analysis, nucleic acid sequencing (such as multiplex sequencing), polymerase chain reaction (such as conventional polymerase chain reaction, and/or quantitative polymerase chain reaction), hybridization of nucleic acid probes, and the like. The nucleic acids can be aligned to references to ascertain the microbial species present in the sample.

Probiotics for Treatment of ASD and/or Schizophrenia

Without being limited by any theory, it is contemplated that the MIA mouse model for autism, which displays both neuropathological and behavioral features of ASD and also schizophrenia, and also exhibits immunological and gastrointestinal abnormalities, is relevant to the corresponding human disorder. It is demonstrated herein that treatment of MIA offspring with human commensal bacteria such as *Bacteroides fragilis* corrects particular gastrointestinal and behavioral deficits in subjects having adult gut microbiota gut signatures. Accordingly, some embodiments include a probiotic treatment and/or prevention for symptoms of ASD and/or schizophrenia in subjects having an adult gut microbiota gut signature.

In some embodiments, the subject is in need of improvement of anxiety, repetitive behavior, and communication behavior (for example, communication, language comprehension and production, and sociability, including vocal and non-vocal social communication). An effective amount of a probiotic comprising, consisting of, or consisting essentially of at least one of the following is provided for administration to the subject (or is for use in treating the subject): (a) *Bacteroides* bacteria (e.g., *B. fragilis*, *B. thetaiotaomicron* or *B. vulgatus*); (b) *Bacteroides* bacteria (e.g., *B. fragilis*, *B. thetaiotaomicron* or *B. vulgatus*) and *Enterococcus* bacteria (e.g., *E. faecilis*, *E. faecium*, *E. hirae*, *E. avium*, *E. durans*, *E. gallinarum*, or *E. casseliflavus*); (c) *B. fragilis*; (d) *B. thetaiotaomicron*; (e) *B. vulgatus*; (g) *B. fragilis* and *B. thetaiotaomicron*; (h) *B. fragilis* and *B. vulgatus*; (i) *B. thetaiotaomicron* and *B. vulgatus*; (j) *B. fragilis*, *B. thetaiotaomicron* and *B. vulgatus*; (k) *B. fragilis* and *Enterococcus* bacteria (e.g., *E. faecilis*, *E. faecium*, *E. hirae*, *E. avium*, *E. durans*, *E. gallinarum*, or *E. casseliflavus*); (l) *B. thetaiotaomicron* and *Enterococcus* bacteria (e.g., *E. faecilis*, *E. faecium*, *E. hirae*, *E. avium*, *E. durans*, *E. gallinarum*, or *E. casseliflavus*); (m) *B. vulgatus* and *Enterococcus* bacteria (e.g., *E. faecilis*, *E. faecium*, *E. hirae*, *E. avium*, *E. durans*, *E. gallinarum*, or *E. casseliflavus*); (n) *B. fragilis* and *B. thetaiotaomicron* and *Enterococcus* bacteria (e.g., *E. faecilis*, *E. faecium*, *E. hirae*, *E. avium*, *E. durans*, *E. gallinarum*, or *E. casseliflavus*); (o) *B. fragilis* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (p) *B. thetaiotaomicron* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (q) *B. fragilis*, *B. thetaiotaomicron* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (r) *B. fragilis* and *E. faecilis*; (s) *B. thetaiotaomicron* and *E. faecilis*; (t) *B. vulgatus* and *E. faecilis*; (u) *B. fragilis* and *B. thetaiotaomicron* and *E. faecilis*; (v) *B. fragilis* and *B. vulgatus* and *E. faecilis*; (w) *B. thetaiotaomicron* and *B. vulgatus* and *E. faecilis*; or (x) *B. fragilis*, *B. thetaiotaomicron*, *B. vulgatus* and *E. faecilis*. Following administration of the bacteria, the anxiety, repetitive behavior, and deficient communication behavior can be improved. Optionally, the subject is identified as having a gut microbiotic signature comprising at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbial phyla as described herein. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject in need of improvement in anxiety, repetitive behavior, and deficient communication behavior has ASD. In some embodiments, the subject in need of improvement in anxiety, repetitive behavior, and communication behavior has schizophrenia. In some embodiments, the communication behavior to be improved comprises at least one of: communication, language comprehension and production, and sociability. In some embodiments, the subject in need of improvement in anxiety, repetitive behavior, and communication behavior is at least three years old, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 years old, including ranges between any two of the listed values.

In some embodiments, the subject is in need of improvement in communication behavior (e.g. language comprehension and/or production, sociability, and/or communication). An effective amount of a probiotic comprising, consisting of, or consisting essentially of at least one of the following is provided for administration to the subject (or is for use in treating the subject): (a) *Bacteroides* bacteria (e.g., *B. fragilis, B. thetaiotaomicron* or *B. vulgatus*); (b) *Bacteroides* bacteria (e.g., *B. fragilis, B. thetaiotaomicron* or *B. vulgatus*) and *Enterococcus* bacteria (e.g., *E. faecilis, E. faecium, E. hirae, E. avium, E. durans, E. gallinarum,* or *E. casseliflavus*); (c) *B. fragilis*; (d) *B. thetaiotaomicron*; (e) *B. vulgatus*; (g) *B. fragilis* and *B. thetaiotaomicron*; (h) *B. fragilis* and *B. vulgatus*; (i) *B. thetaiotaomicron* and *B. vulgatus*; (j) *B. fragilis, B. thetaiotaomicron* and *B. vulgatus*; (k) *B. fragilis* and *Enterococcus* bacteria (e.g., *E. faecilis, E. faecium, E. hirae, E. avium, E. durans, E. gallinarum,* or *E. casseliflavus*); (l) *B. thetaiotaomicron* and *Enterococcus* bacteria (e.g., *E. faecilis, E. faecium, E. hirae, E. avium, E. durans, E. gallinarum,* or *E. casseliflavus*); (m) *B. vulgatus* and *Enterococcus* bacteria (e.g., *E. faecilis, E. faecium, E. hirae, E. avium, E. durans, E. gallinarum,* or *E. casseliflavus*); (n) *B. fragilis* and *B. thetaiotaomicron* and *Enterococcus* bacteria (e.g., *E. faecilis, E. faecium, E. hirae, E. avium, E. durans, E. gallinarum,* or *E. casseliflavus*); (o) *B. fragilis* and *B. vulgatus* and *Enterococcus* bacteria (e.g., *E. faecilis, E. faecium, E. hirae, E. avium, E. durans, E. gallinarum,* or *E. casseliflavus*); (p) *B. thetaiotaomicron* and *B. vulgatus* and *Enterococcus* bacteria (e.g., *E. faecilis, E. faecium, E. hirae, E. avium, E. durans, E. gallinarum,* or *E. casseliflavus*); (q) *B. fragilis, B. thetaiotaomicron* and *B. vulgatus* and *Enterococcus* bacteria (e.g., *E. faecilis, E. faecium, E. hirae, E. avium, E. durans, E. gallinarum,* or *E. casseliflavus*); (r) *B. fragilis* and *E. faecilis*; (s) *B. thetaiotaomicron* and *E. faecilis*; (t) *B. vulgatus* and *E. faecilis*; (u) *B. fragilis* and *B. thetaiotaomicron* and *E. faecilis*; (v) *B. fragilis* and *B. vulgatus* and *E. faecilis*; (w) *B. thetaiotaomicron* and *B. vulgatus* and *E. faecilis*; or (x) *B. fragilis, B. thetaiotaomicron, B. vulgatus* and *E. faecilis*. Following administration of the bacteria, the communication behavior can be improved. Optionally, the subject is identified as having a gut microbiotic signature comprising at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject in need of improvement in communication behavior has ASD. In some embodiments, the subject in need of improvement in communication behavior has schizophrenia. In some embodiments, the communication behavior to be improved comprises at least one of: communication, language comprehension and production, and sociability. In some embodiments, the subject in need of improvement in communication behavior is at least three years old, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 years old, including ranges between any two of the listed values.

In some embodiments, the subject is in need of improvement in repetitive behavior. An effective amount of a probiotic comprising, consisting of, or consisting essentially of at least one of the following is provided for administration to the subject (or is for use in treating the subject): (a) *Bacteroides* bacteria (e.g., *B. fragilis, B. thetaiotaomicron* or *B. vulgatus*); (b) *Bacteroides* bacteria (e.g., *B. fragilis, B. thetaiotaomicron* or *B. vulgatus*) and *Enterococcus* bacteria (e.g., *E. faecilis, E. faecium, E. hirae, E. avium, E. durans, E. gallinarum,* or *E. casseliflavus*); (c) *B. fragilis*; (d) *B. thetaiotaomicron*; (e) *B. vulgatus*; (g) *B. fragilis* and *B. thetaiotaomicron*; (h) *B. fragilis* and *B. vulgatus*; (i) *B. thetaiotaomicron* and *B. vulgatus*; (j) *B. fragilis, B. thetaiotaomicron* and *B. vulgatus*; (k) *B. fragilis* and *Enterococcus* bacteria (e.g., *E. faecilis, E. faecium, E. hirae, E. avium, E. durans, E. gallinarum,* or *E. casseliflavus*); (l) *B. thetaiotaomicron* and *Enterococcus* bacteria (e.g., *E. faecilis, E. faecium, E. hirae, E. avium, E. durans, E. gallinarum,* or *E. casseliflavum*); (m) *B. vulgatus* and *Enterococcus* bacteria (e.g., *E. faecilis, E. faecium, E. hirae, E. avium, E. durans, E. gallinarum,* or *E. casseliflavus*); (n) *B. fragilis* and *B. thetaiotaomicron* and *Enterococcus* bacteria (e.g., *E. faecilis, E. faecium, E. hirae, E. avium, E. durans, E. gallinarum,* or *E. casseliflavus*); (o) *B. fragilis* and *B. vulgatus* and *Enterococcus* bacteria (e.g., *E. faecilis, E. faecium, E. hirae,*

*E. avium, E. durans, E. gallinarum,* or *E. casseliflavus*); (p) *B. thetaiotaomicron* and *B. vulgatus* and *Enterococcus* bacteria (e.g., *E. faecilis, E. faecium, E. hirae, E. avium, E. durans, E. gallinarum,* or *E. casseliflavus*); (q) *B. fragilis, B. thetaiotaomicron* and *B. vulgatus* and *Enterococcus* bacteria (e.g., *E. faecilis, E. faecium, E. hirae, E. avium, E. durans, E. gallinarum,* or *E. casseliflavus*); (r) *B. fragilis* and *E. faecilis*; (s) *B. thetaiotaomicron* and *E. faecilis*; (t) *B. vulgatus* and *E. faecilis*; (u) *B. fragilis* and *B. thetaiotaomicron* and *E. faecilis*; (v) *B. fragilis* and *B. vulgatus* and *E. faecilis*; (w) *B. thetaiotaomicron* and *B. vulgatus* and *E. faecilis*; or (x) *B. fragilis, B. thetaiotaomicron, B. vulgatus* and *E. faecilis*. Following administration of the bacteria, the communication behavior can be improved. Optionally, the subject is identified as having a gut microbiotic signature comprising at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. In some embodiments, the adult gut microbiotic signature is identified as comprising a relative abundance of microbiotic phyla as described herein. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject in need of improvement in repetitive behavior has ASD. In some embodiments, the subject in need of improvement in repetitive behavior has schizophrenia. In some embodiments, the subject in need of improvement in repetitive behavior is at least three years old, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 years old, including ranges between any two of the listed values.

In some embodiments, the subject is in need of improvement in anxiety. An effective amount of a probiotic comprising, consisting of or, consisting essentially of at least one of the following is provided for administration to the subject (or is for use in treating the subject): (a) *Bacteroides* bacteria (e.g., *B. fragilis, B. thetaiotaomicron* or *B. vulgatus*); (b) *Bacteroides* bacteria (e.g., *B. fragilis, B. thetaiotaomicron* or *B. vulgatus*) and *Enterococcus* bacteria (e.g., *E. faecilis, E. faecium, E. hirae, E. avium, E. durans, E. gallinarum,* or *E. casseliflavus*); (c) *B. fragilis*; (d) *B. thetaiotaomicron*; (e) *B. vulgatus*; (g) *B. fragilis* and *B. thetaiotaomicron*; (h) *B. fragilis* and *B. vulgatus*; (i) *B. thetaiotaomicron* and *B. vulgatus*; (j) *B. fragilis, B. thetaiotaomicron* and *B. vulgatus*; (k) *B. fragilis* and *Enterococcus* bacteria (e.g., *E. faecilis, E. faecium, E. hirae, E. avium, E. durans, E. gallinarum,* or *E. casseliflavus*); (l) *B. thetaiotaomicron* and *Enterococcus* bacteria (e.g., *E. faecilis, E. faecium, E. hirae, E. avium, E. durans, E. gallinarum,* or *E. casseliflavus*); (m) *B. vulgatus* and *Enterococcus* bacteria (e.g., *E. faecilis, E. faecium, E. hirae, E. avium, E. durans, E. gallinarum,* or *E. casseliflavus*); (n) *B. fragilis* and *B. thetaiotaomicron* and *Enterococcus* bacteria (e.g., *E. faecilis, E. faecium, E. hirae, E. avium, E. durans, E. gallinarum,* or *E. casseliflavus*); (o) *B. fragilis* and *B. vulgatus* and *Enterococcus* bacteria (e.g., *E. faecilis, E. faecium, E. hirae, E. avium, E. durans, E. gallinarum,* or *E. casseliflavus*); (p) *B. thetaiotaomicron* and *B. vulgatus* and *Enterococcus* bacteria (e.g., *E. faecilis, E. faecium, E. hirae, E. avium, E. durans, E. gallinarum,* or *E. casseliflavus*); (q) *B. fragilis, B. thetaiotaomicron* and *B. vulgatus* and *Enterococcus* bacteria (e.g., *E. faecilis, E. faecium, E. hirae, E. avium, E. durans, E. gallinarum,* or *E. casseliflavus*); (r) *B. fragilis* and *E. faecilis*; (s) *B. thetaiotaomicron* and *E. faecilis*; (t) *B. vulgatus* and *E. faecilis*; (u) *B. fragilis* and *B. thetaiotaomicron* and *E. faecilis*; (v) *B. fragilis* and *B. vulgatus* and *E. faecilis*; (w) *B. thetaiotaomicron* and *B. vulgatus* and *E. faecilis*; or (x) *B. fragilis, B. thetaiotaomicron, B. vulgatus* and *E. faecilis*. Following administration of the bacteria, the communication behavior can be improved. Optionally, the subject is identified as having a gut microbiotic signature comprising at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject in need of improvement in anxiety has ASD. In some embodiments, the subject in need of improvement in anxiety has schizophrenia. In some embodiments, the subject in need of improvement in anxiety is at least three years old, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 years old, including ranges between any two of the listed values.

In some embodiments, the subject is in need of improvement in repetitive behavior and communication behavior (including language comprehension and/or production, sociability, and communication). An effective amount of a probiotic comprising, consisting of or, or consisting essentially of at least one of the following is provided for administration to the subject (or is for use in treating the subject): (a) *Bacteroides* bacteria (e.g., *B. fragilis*, *B. thetaiotaomicron* or *B. vulgatus*); (b) *Bacteroides* bacteria (e.g., *B. fragilis*, *B. thetaiotaomicron* or *B. vulgatus*) and *Enterococcus* bacteria (e.g., *E. faecilis*, *E. faecium*, *E. hirae*, *E. avium*, *E. durans*, *E. gallinarum*, or *E. casseliflavus*); (c) *B. fragilis*; (d) *B. thetaiotaomicron*; (e) *B. vulgatus*; (g) *B. fragilis* and *B. thetaiotaomicron*; (h) *B. fragilis* and *B. vulgatus*; (i) *B. thetaiotaomicron* and *B. vulgatus*; (j) *B. fragilis*, *B. thetaiotaomicron* and *B. vulgatus*; (k) *B. fragilis* and *Enterococcus* bacteria (e.g., *E. faecilis*, *E. faecium*, *E. hirae*, *E. avium*, *E. durans*, *E. gallinarum*, or *E. casseliflavus*); (l) *B. thetaiotaomicron* and *Enterococcus* bacteria (e.g., *E. faecilis*, *E. faecium*, *E. hirae*, *E. avium*, *E. durans*, *E. gallinarum*, or *E. casseliflavus*); (m) *B. vulgatus* and *Enterococcus* bacteria (e.g., *E. faecilis*, *E. faecium*, *E. hirae*, *E. avium*, *E. durans*, *E. gallinarum*, or *E. casseliflavus*); (n) *B. fragilis* and *B. thetaiotaomicron* and *Enterococcus* bacteria (e.g., *E. faecilis*, *E. faecium*, *E. hirae*, *E. avium*, *E. durans*, *E. gallinarum*, or *E. casseliflavus*); (o) *B. fragilis* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (p) *B. thetaiotaomicron* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (q) *B. fragilis*, *B. thetaiotaomicron* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (r) *B. fragilis* and *E. faecilis*; (s) *B. thetaiotaomicron* and *E. faecilis*; (t) *B. vulgatus* and *E. faecilis*; (u) *B. fragilis* and *B. thetaiotaomicron* and *E. faecilis*; (v) *B. fragilis* and *B. vulgatus* and *E. faecilis*; (w) *B. thetaiotaomicron* and *B. vulgatus* and *E. faecilis*; or (x) *B. fragilis*, *B. thetaiotaomicron*, *B. vulgatus* and *E. faecilis*. Following administration of the bacteria, the communication behavior can be improved. Optionally, the subject is identified as having a gut microbiotic signature comprising at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject in need of improvement in repetitive behavior and communication behavior has ASD. In some embodiments, the subject in need of improvement in repetitive behavior and communication behavior has schizophrenia. In some embodiments, the communication behavior to be improved comprises at least one of: communication, language comprehension and production, and sociability. In some embodiments, the subject in need of improvement in repetitive behavior and communication behavior has ASD. In some embodiments, the subject in need of improvement in repetitive behavior and communication behavior has schizophrenia. In some embodiments, the subject in need of improvement in repetitive behavior and communication behavior is at least three years old, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 years old, including ranges between any two of the listed values.

In some embodiments, the subject is in need of improvement in anxiety and communication behavior (including language comprehension and/or production, sociability, and communication). An effective amount of a probiotic comprising, consisting of or, consisting essentially of at least one of the following is provided for administration to the subject (or is for use in treating the subject): (a) *Bacteroides* bacteria (e.g., *B. fragilis*, *B. thetaiotaomicron* or *B. vulgatus*); (b) *Bacteroides* bacteria (e.g., *B. fragilis*, *B. thetaiotaomicron* or *B. vulgatus*) and *Enterococcus* bacteria (e.g., *E. faecilis*, *E. faecium*, *E. hirae*, *E. avium*, *E. durans*, *E. gallinarum*, or *E. casseliflavus*); (c) *B. fragilis*; (d) *B. thetaiotaomicron*; (e) *B. vulgatus*; (g) *B. fragilis* and *B. thetaiotaomicron*; (h) *B. fragilis* and *B. vulgatus*; (i) *B. thetaiotaomicron* and *B. vulgatus*; (j) *B. fragilis*, *B. thetaiotaomicron* and *B. vulgatus*; (k) *B. fragilis* and *Enterococcus* bacteria (e.g., *E. faecilis*, *E. faecium*, *E. hirae*, *E. avium*, *E. durans*, *E. gallinarum*, or *E. casseliflavus*); (l) *B. thetaiotaomicron* and *Enterococcus* bacteria (e.g., *E. faecilis*, *E. faecium*, *E. hirae*, *E. avium*, *E. durans*, *E. gallinarum*, or *E. casseliflavus*); (m) *B. vulgatus* and *Enterococcus* bacteria (e.g., *E. faecilis*, *E. faecium*, *E. hirae*, *E. avium*, *E. durans*, *E. gallinarum*, or *E. casseliflavus*); (n) *B. fragilis* and *B. thetaiotaomicron* and *Enterococcus* bacteria (e.g., *E. faecilis*, *E. faecium*, *E. hirae*, *E. avium*, *E. durans*, *E. gallinarum*, or *E. casseliflavus*); (o) *B. fragilis* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (p) *B. thetaiotaomicron* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (q) *B. fragilis*, *B. thetaiotaomicron* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (r) *B. fragilis* and *E. faecilis*; (s) *B. thetaiotaomicron* and *E. faecilis*; (t) *B. vulgatus* and *E. faecilis*; (u) *B. fragilis* and *B. thetaiotaomicron* and *E. faecilis*; (v) *B. fragilis* and *B. vulgatus* and *E. faecilis*; (w) *B. thetaiotaomicron* and *B.

vulgatus and *E. faecilis*; or (x) *B. fragilis, B. thetaiotaomicron, B. vulgatus* and *E. faecilis*. Following administration of the bacteria, the communication behavior can be improved. Optionally, the subject is identified as having a gut microbiotic signature comprising at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. In some embodiments, the adult gut microbiotic signature is identified as comprising a relative abundance of microbiotic phyla as described herein. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject in need of improvement in anxiety and communication behavior has ASD. In some embodiments, the subject in need of improvement in anxiety and communication behavior has schizophrenia. In some embodiments, the communication behavior to be improved comprises at least one of: communication, language comprehension and production, and sociability. In some embodiments, the subject in need of improvement in anxiety and communication behavior is at least three years old, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 years old, including ranges between any two of the listed values.

In some embodiments, the subject is in need of improvement in anxiety and repetitive behavior. An effective amount of a probiotic comprising, consisting of or, consisting essentially of at least one of the following is provided for administration to the subject (or is for use in treating the subject): (a) *Bacteroides* bacteria (e.g., *B. fragilis, B. thetaiotaomicron* or *B. vulgatus*); (b) *Bacteroides* bacteria (e.g., *B. fragilis, B. thetaiotaomicron* or *B. vulgatus*) and *Enterococcus* bacteria (e.g., *E. faecilis, E. faecium, E. hirae, E. avium, E. durans, E. gallinarum*, or *E. casseliflavus*); (c) *B. fragilis*; (d) *B. thetaiotaomicron*; (e) *B. vulgatus*; (g) *B. fragilis* and *B. thetaiotaomicron*; (h) *B. fragilis* and *B. vulgatus*; (i) *B. thetaiotaomicron* and *B. vulgatus*; (j) *B. fragilis, B. thetaiotaomicron* and *B. vulgatus*; (k) *B. fragilis* and *Enterococcus* bacteria (e.g., *E. faecilis, E. faecium, E. hirae, E. avium, E. durans, E. gallinarum*, or *E. casseliflavus*); (l) *B. thetaiotaomicron* and *Enterococcus* bacteria (e.g., *E. faecilis, E. faecium, E. hirae, E. avium, E. durans, E. gallinarum*, or *E. casseliflavus*); (m) *B. vulgatus* and *Enterococcus* bacteria (e.g., *E. faecilis, E. faecium, E. hirae, E. avium, E. durans, E. gallinarum*, or *E. casseliflavus*); (n) *B. fragilis* and *B. thetaiotaomicron* and *Enterococcus* bacteria (e.g., *E. faecilis, E. faecium, E. hirae, E. avium, E. durans, E. gallinarum*, or *E. casseliflavus*); (o) *B. fragilis* and *B. vulgatus* and *Enterococcus* bacteria (e.g., *E. faecilis, E. faecium, E. hirae, E. avium, E. durans, E. gallinarum*, or *E. casseliflavus*); (p) *B. thetaiotaomicron* and *B. vulgatus* and *Enterococcus* bacteria (e.g., *E. faecilis, E. faecium, E. hirae, E. avium, E. durans, E. gallinarum*, or *E. casseliflavus*); (q) *B. fragilis, B. thetaiotaomicron* and *B. vulgatus* and *Enterococcus* bacteria (e.g., *E. faecilis, E. faecium, E. hirae, E. avium, E. durans, E. gallinarum*, or *E. casseliflavus*); (r) *B. fragilis* and *E. faecilis*; (s) *B. thetaiotaomicron* and *E. faecilis*; (t) *B. vulgatus* and *E. faecilis*; (u) *B. fragilis* and *B. thetaiotaomicron* and *E. faecilis*; (v) *B. fragilis* and *B. vulgatus* and *E. faecilis*; (w) *B. thetaiotaomicron* and *B. vulgatus* and *E. faecilis*; or (x) *B. fragilis, B. thetaiotaomicron, B. vulgatus* and *E. faecilis*. Following administration of the bacteria, the communication behavior can be improved. Optionally, the subject is identified as having a gut microbiotic signature comprising at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients. Optionally, the *B. fragilis* comprises wild-type *B. fragilis*, mutant *B. fragilis* lacking polysaccharide A (dPSA), or a combination of wild-type *B. fragilis* and dPSA *B. fragilis*. Optionally, the *B. fragilis* comprises wild-type *B. fragilis*, mutant *B. fragilis* lacking polysaccharide A (dPSA), or a combination of wild-type *B. fragilis* and dPSA *B. fragilis*. In some embodiments, the subject in need of improvement in anxiety and repetitive behavior has ASD. In some embodiments, the subject in need of improvement in anxiety and repetitive behavior has schizophrenia. In some embodiments, the subject in need of improvement in anxiety and repetitive behavior is at least three years old, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 years old, including ranges between any two of the listed values.

In some embodiments, the probiotic comprises any of the above-disclosed bacterial species or combinations of bacterial species, and is provided for administration to the subject (or is for administration to the subject) in a single probiotic composition. In some embodiments, the probiotic comprises any of the above-referenced bacterial species or combinations of bacterial species, and is administered to the subject (or is for administration to the subject) in two or more different probiotic compositions. For example, a probiotic of "bacteria A and bacteria B" can be administered either in a single composition comprising bacteria A and bacteria B, or in a first composition comprising bacteria A in conjunction with a second composition comprising bacteria B. In some embodiments, first and second compositions are administered simultaneously. In some embodiments, the first and second compositions are administered separately.

In some embodiments, a probiotic comprising a combination of *Bacteroides* bacteria as described herein is provided as a first composition comprising a first *Bacteroides* bacterium or combination of *Bacteroides* bacteria, and a second composition comprising a second *Bacteroides* bacterium or combination of *Bacteroides* bacteria as described herein. In some embodiments, a probiotic comprising a combination of *Enterococcus* bacteria and *Bacteroides* bacteria as described herein is provided as a first composition comprising the *Enterococcus* bacteria, and a second composition comprising the *Bacteroides* bacteria or combination of *Bacteroides* bacteria as described herein. In some embodiments, the *Enterococcus* bacteria and a first *Bacteroides* bacteria (or combination of *Bacteroides* bacteria) are administered in a first composition, and the *Enterococcus* bacteria and a second *Bacteroides* bacteria (or combination of *Bacteroides* bacteria) that is different from the first are administered in a second composition. In some embodiments, the *Enterococcus* bacteria and a first *Bacteroides* bacteria (or combination of *Bacteroides* bacteria) are administered in a first composition, and a second *Bacteroides* bacteria (or combination of *Bacteroides* bacteria) that is different from the first is administered in a second composition.

In accordance with any of the embodiments described above, optionally, each composition, use, or method is free of, or is substantially free of bacteria other than the identified bacteria of the probiotic. In accordance with any of the embodiments described above, optionally, each composition is free of, or is substantially free of antibiotics. In accordance with any of the embodiments described above, optionally, each composition is free of, or is substantially free of bacteria other than the probiotic and antibiotics.

In accordance with embodiments described herein, the probiotics of the methods, uses, and compositions described herein can be for any suitable route of administration. For example, the probiotic can be administered to the subject via oral administration, rectum administration, transdermal administration, intranasal administration or inhalation. In some embodiments, the probiotic is administered to the subject orally.

In some embodiments, the effective amount of bacteria in the probiotic composition, use, or method includes at least about $10^4$ colony forming units (cfu), for example at least about $10^4$, $10^5$, $10^6$, $10^7$, $10^8$, $10^9$, $10^{10}$, $10^{11}$, $10^{12}$, or $10^{13}$ cfu, including ranges between any of the listed values, for example $10^4$-$10^8$ cfu, $10^4$-$10^9$ cfu, $10^4$-$10^{10}$ cfu, $10^4$-$10^{11}$ cfu, $10^4$-$10^{12}$ cfu, $10^4$-$10^{12}$ cfu, $10^5$-$10^8$ cfu, $10^5$-$10^9$ cfu, $10^5$-$10^{10}$ cfu, $10^5$-$10^{11}$ cfu, $10^5$-$10^{12}$ cfu, $10^5$-$10^{12}$ cfu, $10^6$-$10^8$ cfu, $10^6$-$10^9$ cfu, $10^6$-$10^{10}$ cfu, $10^6$-$10^{11}$ cfu, $10^6$-$10^{12}$ cfu, $10^6$-$10^{12}$ cfu, $10^7$-$10^8$ cfu, $10^7$-$10^9$ cfu, $10^7$-$10^{10}$ cfu, $10^7$-$10^{11}$ cfu, $10^7$-$10^{12}$ cfu, $10^7$-$10^{12}$ cfu, $10^8$-$10^9$ cfu, $10^8$-$10^{10}$ cfu, $10^8$-$10^{11}$ cfu, $10^8$-$10^{12}$ cfu, or $10^8$-$10^{12}$ cfu. In some embodiments, the effective amount of bacteria comprises a log phase quantity (at 37° C.) of bacteria in a composition for administration to the subject. In some embodiments, the effective amount of bacteria comprises a stationary phase quantity (at 37° C.) of bacteria in a composition for administration to the subject.

Methods of Treating and/or Preventing Symptoms of ASD and/or Schizophrenia

In some embodiments, methods of treating ASD and/or schizophrenia symptoms are provided. The method can comprise identifying the subject can as in need of improving an anxiety, repetitive behavior, and/or communication behavior. Optionally, the method can comprise determining a gut microbiotic signature of the subject from a sample of the subject. Optionally, the subject is determined to be amenable to the method of treatment if the gut microbiotic signature of the subject comprises at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. The method can comprising administering an effective amount of a probiotic comprising, consisting essentially or, consisting of *Enterococcus* bacteria, *Bacteroides* bacteria, or a combination of *Enterococcus* bacteria and *Bacteroides* bacteria as described herein is administered to the subject in need of behavioral improvement. The subject can exhibit improved anxiety, repetitive behavior, or communication behavior following administration of the probiotic. In some embodiments, the subject is in need of improved anxiety, and following administration of the probiotic, anxiety is improved. In some embodiments, the subject is in need of improved communication behavior, and following administration of the probiotic, communication behavior is improved. In some embodiments, the subject is in need of improved anxiety and repetitive behavior, and following administration of the probiotic, communication behavior is improved. In some embodiments, the subject is in need of improved anxiety and communication behavior, and following administration of the probiotic, communication behavior is improved. In some embodiments, the subject is in need of improved repetitive behavior and communication behavior, and following administration of the probiotic, communication behavior is improved. In some embodiments, the communication behavior in need of improvement (and that is improved after administration of the probiotic) comprises at least one of communication, sociability, or language comprehension and/or language production. In some embodiments, the subject is further identified as in need of improvement of defects in intestinal barrier integrity, and following administration of the probiotic, the defects in defects in intestinal barrier integrity are improved. Optionally the subject is at least three years old.

In some embodiments, methods of treating ASD symptoms are provided. The method can comprise identifying a subject as in need of improving anxiety, repetitive behavior, and/or communication behavior. Optionally, the method can comprise determining a gut microbiotic signature of the subject from a sample of the subject. Optionally, the subject is determined to be amenable to the method of treatment if the gut microbiotic signature of the subject comprises at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. The method can comprise administering a probiotic comprising, consisting essentially of, or consisting of an effective amount of *Bacteroides* bacteria, or a combination of *Bacteroides* and *Enterococcus* bacteria as described herein. The anxiety, repetitive behavior, and/or communication behavior can be improved following administration of the probiotic. In some embodiments, the method comprises determining the subject to be in need of improving anxiety and repetitive behavior. Following administration of the probiotic, anxiety and repetitive behavior can be improved. Optionally the subject is at least three years old. In some embodiments, the method comprises determining the subject to be in need of improving anxiety and communication behavior. Following administration of the probiotic, anxiety and communication behavior can be improved. In some embodiments, the method comprises determining the subject to be in need of improving repetitive behavior and communication behavior. Following administration of probiotic, the repetitive behavior and communication behavior are improved. In some embodiments, the method comprises determining the subject to be in need of improving anxiety, communication behavior, and repetitive behavior, and following administration of the probiotic, anxiety, communication behavior, and repetitive behavior are improved. In some embodiments, the communication behavior in need of improvement (and subsequently improved) comprises at least one of communication, sociability, or language comprehension and/or language production. In some embodiments, the method further comprises determining whether or not the subject has ASD. In some embodiments, the ASD symptoms are treated. In some embodiments, the subject is further identified as in need of improvement of defects in intestinal barrier integrity, and following administration of the probiotic, the defects in defects in intestinal barrier integrity are improved.

In some embodiments, methods of treating schizophrenia symptoms are provided. The method can comprise identifying a subject as in need of improving anxiety, repetitive behavior, and/or communication behavior. Optionally, the method can comprise determining a gut microbiotic signature of the subject from a sample of the subject. Optionally, the subject is determined to be amenable to the method of treatment if the gut microbiotic signature of the subject comprises at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. The method can comprise administering a probiotic comprising, consisting essentially of, or consisting of an effective amount of *Bacteroides* bacteria, or a combination of *Bacteroides* and *Enterococcus* bacteria as described herein. The anxiety, repetitive behavior, and/or communication behavior can be improved following administration of the probiotic. In some embodiments, the method comprises determining the subject to be in need of improving anxiety and repetitive behavior. Following administration of the probiotic, anxiety and repetitive behavior can be improved. Optionally the subject is at least three years old.

In some embodiments, the method comprises determining the subject to be in need of improving anxiety and communication behavior. Following administration of the probiotic, anxiety and communication behavior can be improved. In some embodiments, the method comprises determining the subject to be in need of improving repetitive behavior and communication behavior. Following administration of probiotic, the repetitive behavior and communication behavior are improved. In some embodiments, the method comprises determining the subject to be in need of improving anxiety, communication behavior, and repetitive behavior, and following administration of the probiotic, anxiety, communication behavior, and repetitive behavior are improved. In some embodiments, the communication behavior in need of improvement (and subsequently improved) comprises at least one of communication, sociability, or language comprehension and/or language production. In some embodiments, the method further comprises determining whether or not the subject has schizophrenia. In some embodiments, the schizophrenia symptoms are treated. In some embodiments, the subject is further identified as in need of improvement of defects in intestinal barrier integrity, and following administration of the probiotic, the defects in defects in intestinal barrier integrity are improved.

In some embodiments, methods of preventing ASD and/or schizophrenia symptoms are provided. The method can comprise identifying a subject as at risk of developing anxiety, repetitive behavior, and/or deficient communication behavior. Optionally, the method can comprise determining a gut microbiotic signature of the subject from a sample of the subject. Optionally, the subject is determined to be amenable to the method of treatment if the gut microbiotic signature of the subject comprises at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. The method can comprise administering a probiotic comprising, consisting essentially of, or consisting of an effective amount of *Bacteroides* bacteria, or a combination of *Bacteroides* and *Enterococcus* bacteria as described herein. The subject can develop with minimized deficiencies or no discernable deficiencies in anxiety, repetitive behavior, and/or communication behavior. In some embodiments, the subject is determined to be at risk for developing anxiety. Following administration of the probiotic, the subject can develop with minimal or no anxiety. Optionally, the at-risk subject is a child, adolescent, or adult three years old or older. In some embodiments, the subject is determined to be at risk for developing repetitive behavior. Following administration of the probiotic, the subject can develop with minimal or no repetitive behavior. In some embodiments, the subject is determined to be at risk for developing deficient communication behavior. Following administration of the probiotic, the subject can develop with minimal or no deficiencies in communication behavior. In some embodiments, the communication behavior that develops without discernable deficiencies includes at least one of language comprehension and/or production, sociability, or communication. In some embodiments, the method further comprises determining whether the subject is at risk for ASD. In some embodiments, ASD symptoms are prevented. In some embodiments, the method further comprises determining whether the subject is at risk for schizophrenia. In some embodiments, schizophrenia symptoms are prevented. In some embodiments, ASD and schizophrenia symptoms are prevented.

In some embodiments, methods of preventing ASD symptoms are provided. The method can comprise identifying a subject as at risk of developing anxiety, repetitive behavior, and/or deficient communication behavior. Optionally, the method can comprise determining a gut microbiotic signature of the subject from a sample of the subject. Optionally, the subject is determined to be amenable to the method of treatment if the gut microbiotic signature of the subject comprises at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. The method can comprise administering a probiotic comprising, consisting essentially of, or consisting of an effective amount of *Bacteroides* bacteria, or a combination of *Bacteroides* and *Enterococcus* bacteria as described herein. The subject can develop with minimized deficiencies or no discernable deficiencies in anxiety, repetitive behavior, and/or communication behavior. Optionally, the at-risk subject is a child, adolescent, or adult three years old or older. In some embodiments, the subject is determined to be at risk for developing anxiety. Following administration of the probiotic, the subject can develop with minimal or no anxiety. In some embodiments, the subject is determined to be at risk for developing repetitive behavior. Following administration of the probiotic, the subject can develop with minimal or no repetitive behavior. In some embodiments, the subject is determined to be at risk for developing deficient communication behavior. Following administration of the probiotic, the subject can develop with minimal or no deficiencies in communication behavior. In some embodiments, the communication behavior that develops without discernable deficiencies includes at least one of language comprehension and/or production, sociability, or communication. In some embodiments, the method further comprises determining whether the subject is at risk for ASD. In some embodiments, ASD symptoms are prevented.

In some embodiments, methods of preventing schizophrenia symptoms are provided. The method can comprise identifying a subject as at risk of developing anxiety, repetitive behavior, and/or deficient communication behavior. Optionally, the method can comprise determining a gut microbiotic signature of the subject from a sample of the subject. Optionally, the subject is determined to be amenable to the method of treatment if the gut microbiotic signature of the subject comprises at least 500 different species of microbes, for example at least 500, 600, 700, 800, 900, 1000, 111, 1200, 1300, 1400, or 1500 different species, including ranges between any two of the listed values. Optionally the subject is identified as having an adult gut microbiotic signature. Optionally, the adult gut microbiotic signature is identified based on relative quantities of particular microbiotic phyla as described herein. The method can comprise administering a probiotic comprising, consisting essentially of, or consisting of an effective amount of *Bacteroides* bacteria, or a combination of *Bacteroides* and *Enterococcus* bacteria as described herein. The subject can develop with minimized deficiencies or no discernable deficiencies in anxiety, repetitive behavior, and/or communication behavior. Optionally, the at-risk subject is a child, adolescent, or adult three years old or older. In some embodiments, the subject is determined to be at risk for developing anxiety. Following administration of the probiotic, the subject can develop with minimal or no anxiety. In some embodiments, the subject is determined to be at risk for developing repetitive behavior. Following administration of the probiotic, the subject can develop with minimal or no repetitive behavior. In some embodiments, the subject is determined to be at risk for developing deficient communication behavior. Following administration of the probiotic, the subject can develop with minimal or no deficiencies in communication behavior. In some embodiments, the communication behavior that develops without discernable deficiencies includes at least one of language comprehension and/or production, sociability, or communication. In some embodiments, the method further comprises determining whether the subject is at risk for schizophrenia. In some embodiments, schizophrenia symptoms are prevented.

In some embodiments, in accordance with any of the methods described above, the gut microbiotic signature of the subject is determined by analyzing nucleic acids in a sample from the subject using a suitable method known to one skilled in the art. For example, sequences of nucleic acids in the samples can be ascertained to determine the number of different species of microbes in the gut. For example, the nucleic acids from the sample can be sequenced using multiplex sequencing. For example, the nucleic acids can be analyzed on a microarray. For example, the nucleic acids can be analyzed by polymerase chain reaction (conventional or quantitative). For example, the nucleic acids can be analyzed by hybridization of a nucleic acid probe. Optionally, the nucleic acid sequences are compared to a reference, for example a nucleic acid database to ascertain the microbial species of origin. Optionally, the nucleic acids comprise the ribosomal RNA 16s subunit. Optionally, nucleic acids are isolated from the sample before their sequences are ascertained. Optionally, the nucleic acids from the sample are pooled, so that the sequences of a population of microbes can be ascertained from the pooled nucleic acids (e.g. via multiplex analysis). In some embodiments, the sample comprises a fecal sample.

In some embodiments, in accordance with any of the methods described above, the probiotic comprising, consisting essentially or, consisting of *Bacteroides* bacteria, or a combination of *Enterococcus* bacteria and *Bacteroides* bacteria of any of the methods described herein is selected from the group consisting of (a) *Bacteroides* bacteria (e.g., *B. fragilis*, *B. thetaiotaomicron* or *B. vulgatus*); (b) *Bacteroides* bacteria (e.g., *B. fragilis*, *B. thetaiotaomicron* or *B. vulgatus*) and *Enterococcus* bacteria (e.g., *E. faecilis*, *E. faecium*, *E. hirae*, *E. avium*, *E. durans*, *E. gallinarum*, or *E. casseliflavus*); (c) *B. fragilis*; (d) *B. thetaiotaomicron*; (e) *B. vulgatus*; (g) *B. fragilis* and *B. thetaiotaomicron*; (h) *B. fragilis* and *B. vulgatus*; (i) *B. thetaiotaomicron* and *B. vulgatus*; (j) *B. fragilis*, *B. thetaiotaomicron* and *B. vulgatus*; (k) *B. fragilis* and *Enterococcus* bacteria (e.g., *E. faecilis*, *E. faecium*, *E. hirae*, *E. avium*, *E. durans*, *E. gallinarum*, or *E. casseliflavus*); (l) *B. thetaiotaomicron* and *Enterococcus* bacteria (e.g., *E. faecilis*, *E. faecium*, *E. hirae*, *E. avium*, *E. durans*, *E. gallinarum*, or *E. casseliflavus*); (m) *B. vulgatus* and *Enterococcus* bacteria (e.g., *E. faecilis*, *E. faecium*, *E. hirae*, *E. avium*, *E. durans*, *E. gallinarum*, or *E. casseliflavus*); (n) *B. fragilis* and *B. thetaiotaomicron* and *Enterococcus* bacteria (e.g., *E. faecilis*, *E. faecium*, *E. hirae*, *E. avium*, *E. durans*, *E. gallinarum*, or *E. casseliflavus*); (o) *B. fragilis* and *B. vulgatus* and *Enterococcus* bacteria (e.g., *E. faecilis*, *E. faecium*, *E. hirae*, *E. avium*, *E. durans*, *E. gallinarum*, or *E. casseliflavus*); (p) *B. thetaiotaomicron* and *B. vulgatus* and *Enterococcus* bacteria (e.g., *E. faecilis, E. faecium, E. hirae, E. avium, E. durans, E. gallinarum,* or *E. casseliflavus*); (q) *B. fragilis, B. thetaiotaomicron* and *B. vulgatus* and *Enterococcus* bacteria (e.g., *E. faecilis, E. faecium, E. hirae, E. avium, E. durans, E. gallinarum,* or *E. casseliflavus*); (r) *B. fragilis* and *E. faecilis*; (s) *B. thetaiotaomicron* and *E. faecilis*; (t) *B. vulgatus* and *E. faecilis*; (u) *B. fragilis* and *B. thetaiotaomicron* and *E. faecilis*; (v) *B. fragilis* and *B. vulgatus* and *E. faecilis*; (w) *B. thetaiotaomicron* and *B. vulgatus* and *E. faecilis*; or (x) *B. fragilis, B. thetaiotaomicron, B. vulgatus* and *E. faecilis*. Optionally, the subject is administered no other bacteria, or substantially no other bacteria apart from the identified bacteria of the probiotic, and as such the probiotic for use in treatment of the subject is in a composition or compositions free or substantially free of other bacteria. Optionally, the subject is administered no antibiotics, or is administered substantially no antibiotics, and as such the probiotic for administration to the subject is in a composition or compositions free or substantially free of antibiotics. Optionally, the subject is administered no drugs, or is administered substantially no drugs, and as such the probiotic for administration to the subject is in a composition or compositions free or substantially free of drugs. Optionally, the subject is administered no pharmaceutically active ingredients, or is administered substantially no pharmaceutically active ingredients, and as such the probiotic for administration to the subject is in a composition or compositions free or substantially free of pharmaceutically active ingredients.

In some embodiments, in accordance with any of the methods described above, the determination that the subject is in need of improving a behavior is made according to at least one of a behavioral assessment and/or determination of the presence, absence, and/or level of at least one biological marker from a sample of the subject. In some embodiments, for example uses, methods, and or compositions directed to infants and/or children, a subject at risk for an ASD behavior is identified based on maternal immune activation and/or other risk factors. In some embodiments, the subject is diagnosed as having ASD based on the level of an ASD-related metabolite or combination of metabolites in the gut, in a bodily fluid (for example, blood and urine), or any combination thereof. Methods of diagnosing ASD based on levels of metabolite in a subject are described in detail in US Pub. No. 2014/0065132, hereby incorporated by reference in its entirety. In some embodiments, the subject is determined to have a lesion or developmental deficiency in a region of the brain associated with speech production, speech recognition, impulse control, and/or socialization, for example regions of the cerebral cortex, the corpus colosum, Broca's area, and/or Wernicke's area. In some embodiments, an ASD behavior, for example a deficient communication, vocalization, sensorimotor, anxiety, and/or repetitive behavior, or a combination of two or more of these is identified using standard diagnostic criteria, for example in the Diagnostic and Statistical Manual of Mental Disorders, Fourth Edition (DSM-4) or Fifth Edition (DSM-5). In some embodiments, the presence or absence of ASD in the subject is determined using a behavioral test, for example at least one of the Autism Behavior Checklist (ABC), Autism diagnostic Interview-Revised (ADI-R), childhood autism Rating Scale (CARS), and/or Pre-Linguistic Autism Diagnostic Observation Schedule (PL-ADOS). The behavioral test can include, but is not limited to, detecting the presence and/or extent of 1) preoccupation with one or more stereotyped and restricted patterns of interest that is abnormal in either intensity or focus, 2) inflexible adherence to specific, nonfunctional routines or rituals, c) stereotyped and repetitive motor mannerisms (such as hand flapping, finger flapping etc.), and/or d) persistent preoccupation with parts of objects. Non-limiting examples of behavior that can be included in a behavioral test and suggest a need for improving behavioral performance in the subject under the test include: a) sensory behaviors, including poor use of visual discrimination when learning, seems not to hear, so that a hearing loss is suspected, sometimes shows no "startle response" to loud noise", sometimes painful stimuli such as bruises, cuts, and injections evoke no reaction, often will not blink when bright light is directed toward eyes, covers ears at many sounds, squints, frowns, or covers eyes when in the presence of natural light, frequently has no visual reaction to a "new" person, stares into space for long periods of time; b) relating behaviors: frequently does not attend to social/environmental stimuli, has no social smile, does not reach out when reached for, non-responsive to other people's facial expressions/feelings, actively avoids eye contact, resists being touched or held, is flaccid when held in arms, is stiff and hard to held, does not imitate other children at play, has not developed any friendships, often frightened or very anxious, "looks through" people; c) body and object use behaviors: whirls self for long periods of time, does not use toys appropriately, insists on keeping certain objects with him/her, rocks self for long periods of time, does a lot of lunging and darting, flaps hands, walks on toes, hurts self by banging head, biting hand, twirls, spins, and bangs objects a lot, feel, smell, and/or taste objects in the environment, gets involved in complicated "rituals" such as lining things up, is very destructive; and d) language behaviors: does not follow simple commands given once, has pronoun reversal, speech is atonal, does not respond to own name when called out among two others, seldom says "yes" or "I", does not follow simple commands involving prepositions, gets desired objects by gesturing, repeats phrases over and over, cannot point to more than five named objects, uses 0-5 spontaneous words per day to communicate wants and needs, repeats sounds or words over and over, echoes questions or statements made by others, uses at least 15 but less than 30 spontaneous phrases daily to communicate, learns a simple task but "forgets" quickly, strong reactions to changes in routine/environment, has "special abilities" in one area of development, which seems to rule out mental retardation, severe temper tantrums and/or frequent minor tantrums, hurts others by biting, hitting, and/or kicking, does not wait for needs to be met, difficulties with toileting, does not dress self without frequent help, frequently unaware of surroundings, and may be oblivious to dangerous situations, prefers to manipulate and be occupied with inanimate things, and/or a developmental delay identified at or before 30 months of age. One of ordinary skill in the art would appreciate that the attending physician would know how to identify a subject in need of treatment disclosed herein.

In some embodiments, in accordance with any of the methods described above, the method comprises administering the effective amount of probiotic in a single administration of one or more compositions. In some embodiments as described above, the method comprises administering the effective amount of the probiotic across two or more administrations of a single composition as described herein. For example, the compositions can be administered about 1 minute, 2, 3, 4, 5, 6, 7, 8, 9, 10, 15, 20, 25, 30, 35, 40, 45, 50, 55 minutes, 1 hour, 2, 3, 4, 5, 6, 7, 8, 9, 10, 11, 12, 13, 14, 15, 16, 17, 18, 19, 20, 21, 22, 23 hours, 1 day, 2, 3, 4, 5, 6, 7, 8, 9, or 10 days apart, including ranges between any two of the listed values, for example 1 minute-10 minutes, 1 minute to 30 minutes, 1 minute to 1 hour, 1 minute-2 hours, 1 minute-4 hours, 1 minute-12 hours, 1 minute-18 hours, 1 minute-1 day, 10 minutes to 30 minutes, 10 minutes to 1 hour, 10 minutes-2 hours, 10 minutes-4 hours, 10 minute-12 hours, 10 minutes-18 hours, 10 minutes-1 day, 30 minutes to 1 hour, 30 minutes-2 hours, 30 minutes-4 hours, 30 minute-12 hours, 30 minutes-18 hours, 30 minutes-1 day, 30 minutes-2 days, 1 hour-2 hours, 1 hour-4 hours, 1 hour-12 hours, 1 hour-18 hours, 1 hour-1 day, 4 hours-12 hours, 4 hours-18 hours, 4 hours-1 day, 1 day-2 days, 1 day-3 days, 1 day-4 days, 1 day-5 days, 1 day-7 days, 1 day-10 days, 2 days-3 days, 2 days-4 days, 2 days-5 days, 2 days-7 days, 2 days-10 days, or 5 days to 10 days. In some embodiments as described above, the method comprises administering the effective amount of two or more different compositions as described herein across two or more administrations of a single composition. For example, the second composition can be administered about 1 minute, 2, 3, 4, 5, 6, 7, 8, 9, 10, 15, 20, 25, 30, 35, 40, 45, 50, 55 minutes, 1 hour, 2, 3, 4, 5, 6, 7, 8, 9, 10, 11, 12, 13, 14, 15, 16, 17, 18, 19, 20, 21, 22, 23 hours, 1 day, 2, 3, 4, 5, 6, 7, 8, 9, or 10 days after the first composition, including ranges between any two of the listed values, for example 1 minute-10 minutes, 1 minute to 30 minutes, 1 minute to 1 hour, 1 minute-2 hours, 1 minute-4 hours, 1 minute-12 hours, 1 minute-18 hours, 1 minute-1 day, 10 minutes to 30 minutes, 10 minutes to 1 hour, 10 minutes-2 hours, 10 minutes-4 hours, 10 minute-12 hours, 10 minutes-18 hours, 10 minutes-1 day, 30 minutes to 1 hour, 30 minutes-2 hours, 30 minutes-4 hours, 30 minute-12 hours, 30 minutes-18 hours, 30 minutes-1 day, 30 minutes-2 days, 1 hour-2 hours, 1 hour-4 hours, 1 hour-12 hours, 1 hour-18 hours, 1 hour-1 day, 4 hours-12 hours, 4 hours-18 hours, 4 hours-1 day, 1 day-2 days, 1 day-3 days, 1 day-4 days, 1 day-5 days, 1 day-7 days, 1 day-10 days, 2 days-3 days, 2 days-4 days, 2 days-5 days, 2 days-7 days, 2 days-10 days, or 5 days to 10 days. In some embodiments, the probiotic is administered in a slow release formulation (for example a slow-release capsule or implant) for any of the durations described above.

In some embodiments, the probiotic is administered to the subject until an improvement in behavioral performance is observed. Optionally, the probiotic is administered to the subject after an improvement in behavioral performance is observed, for example to solidify or maintain the improved behavioral performance.

EXAMPLES

Some aspects of the embodiments discussed above are disclosed in further detail in the following examples, which are not in any way intended to limit the scope of the present disclosure.

Figure 1B:
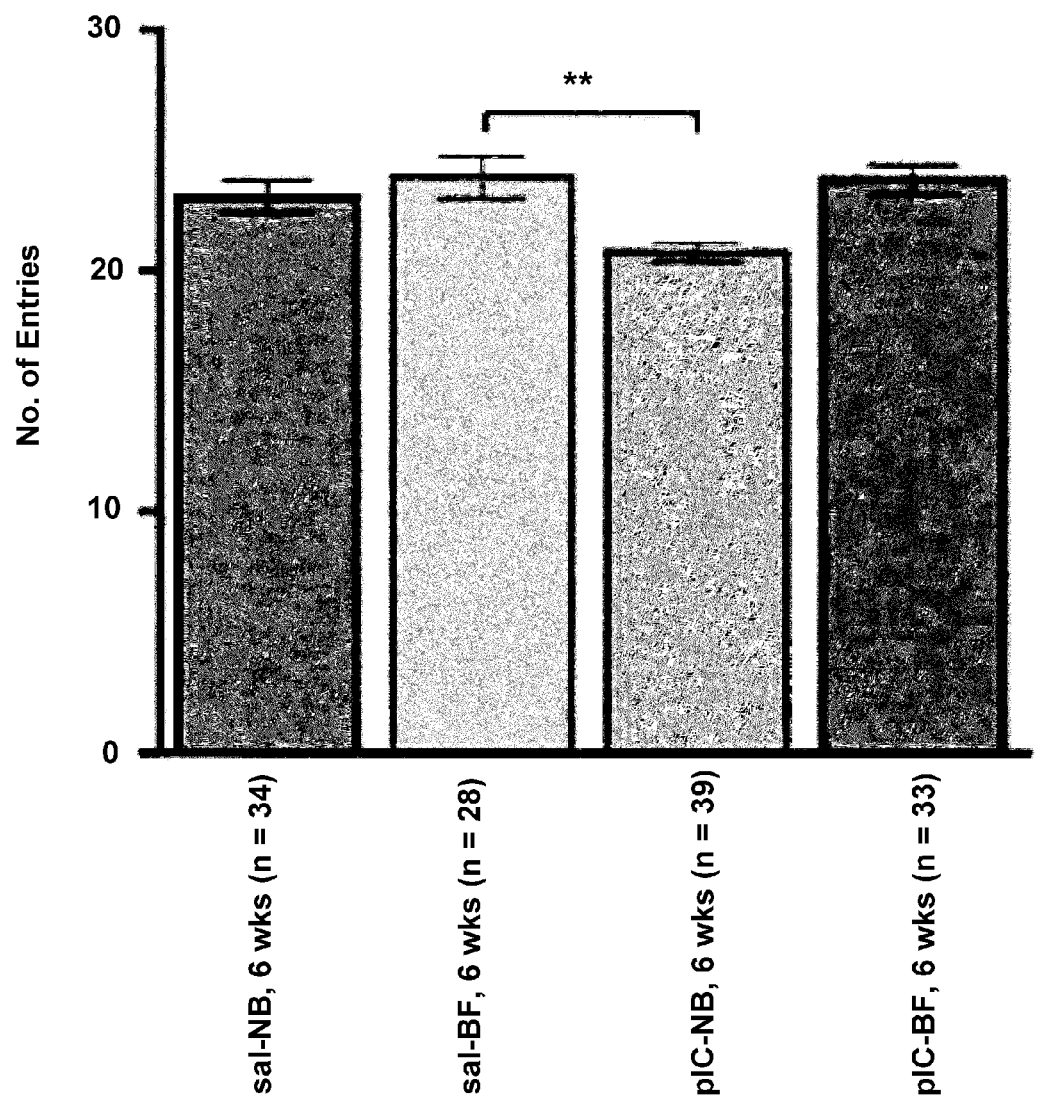

Example 1: Adult Treatment Demonstrating Treatment of Adult MIA Mice with a Probiotic Comprising *B. fragilis* Corrects Deficits in Exploratory Behavior 6-week-old offspring of immune-activated mothers were given applesauce containing *B. fragilis* or applesauce alone for 1 week. 4 weeks after bacterial treatment, mice were tested for anxiety-like and exploratory behavior in the open field exploration assay. Adult treatment with *B. fragilis* significantly increased exploratory behavior in MIA offspring, as measured by increased entries into the center arena (FIG. 1A) and increased total distance traveled in the open arena (FIG. 1B). Poly(I:C) was administered as an immune activator in mothers. Offspring of non-immune activated mothers (saline treatment) were examined as additional controls. Abbreviations used in FIGS. 1A-1B: Sal=saline offspring controls, pIC=poly(I:C) offspring, NB=sodium bicarbonate vehicle, BF=*B. fragilis*.

Anxiety-like and exploratory behavior, as measured by entries into center area and total distance traveled in open area were significantly higher in the *B. fragilis*-treated adult offspring of immune-activated mothers than in untreated controls. The treated offspring would be understood to have an adult gut microbiome signature. Accordingly, treatment with a probiotic comprising, consisting essentially of, or consisting of *B. fragilis* can improve anxiety-like behavior and exploratory behavior in subjects having adult gut microbiomes and exhibiting ASD symptoms in accordance with some embodiments described herein.

Figure 2:
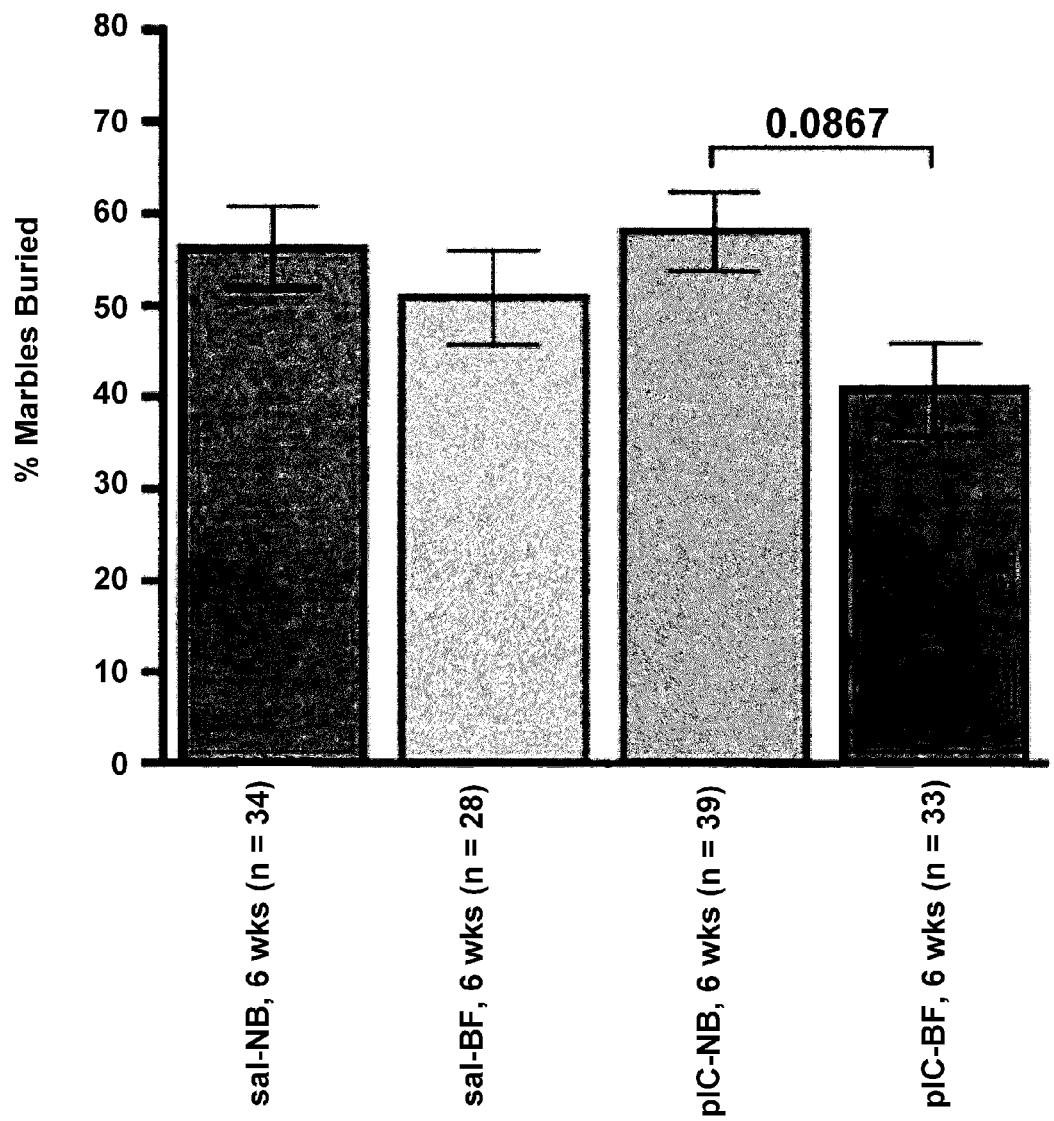
FIG. 2 is a graph demonstrating that treatment of adult MIA mice with a probiotic comprising *B. fragilis* reduces repetitive behavior in accordance with some embodiments described herein.
Figure 3:
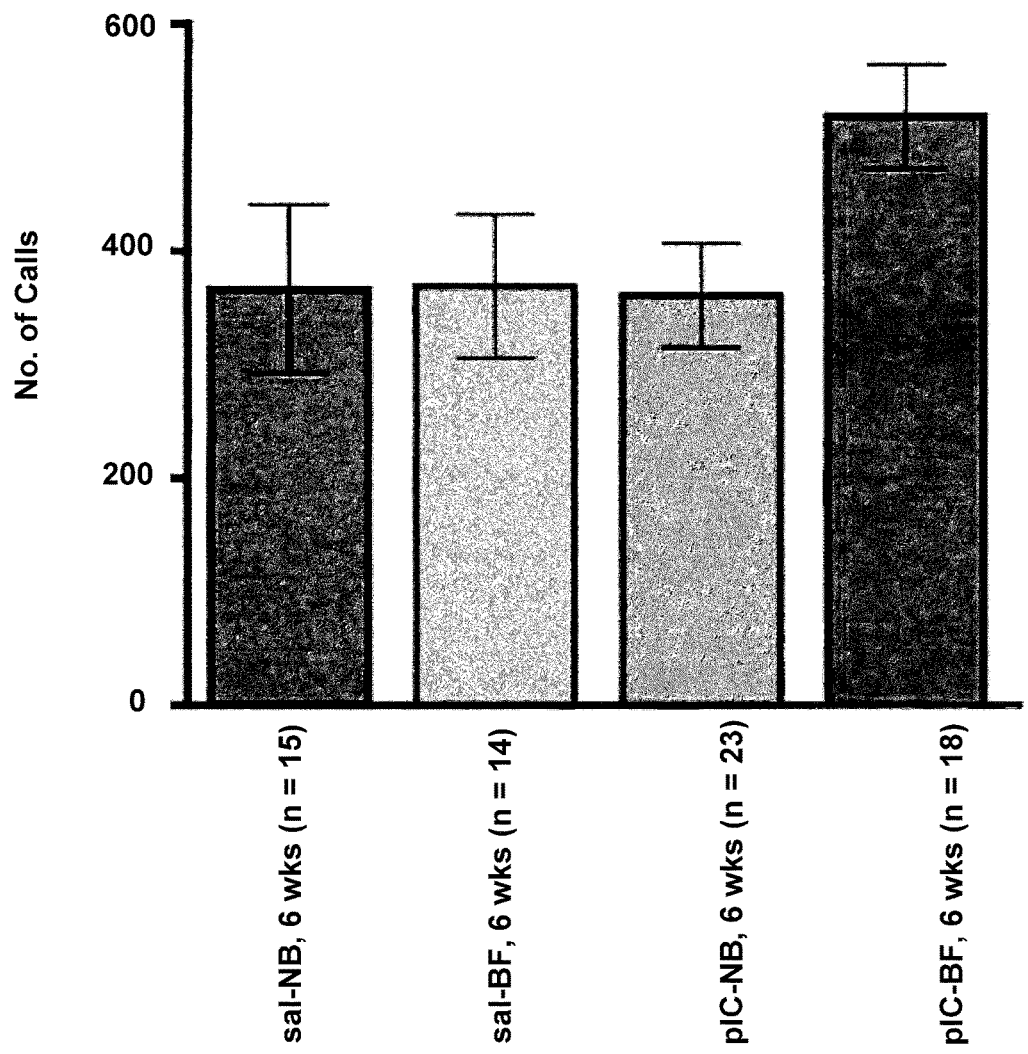
FIG. 3 is a graph demonstrating that treatment of adult MIA mice with a probiotic comprising *B. fragilis* increases communication behavior in accordance with some embodiments described herein.

Example 2: Adult Treatment Demonstrating Treatment of Adult MIA Mice with a Probiotic Comprising *B. fragilis* Reduces Repetitive Behavior in Accordance with Some Embodiments Described Herein 6-week-old offspring of immune-activated mothers were given applesauce containing *B. fragilis* or applesauce alone for 1 week. 4 weeks after bacterial treatment, mice were tested for repetitive behavior in a stereotyped marble burying assay. As shown in FIG. 2, Adult treatment with *B. fragilis* decreased stereotyped marble burying in MIA offspring as compared to untreated controls. Poly(I:C) was administered as an immune activator in mothers. Offspring of non-immune activated mothers (saline treatment) were examined as additional controls. Abbreviations used in FIG. 2: Sal=saline offspring controls, pIC=poly(I:C) offspring, NB=sodium bicarbonate vehicle, BF=*B. fragilis*. To test for statistical significance, a p value for a one way analysis of variance (ANOVA) with Bonferroni post hoc test was performed (shown p=0.0867).

Repetitive behavior, as measured by the marble burying test was reduced in the *B. fragilis*-treated adult offspring of immune-activated mothers than in untreated controls. Accordingly, treatment with a probiotic comprising, consisting essentially of, or consisting of *B. fragilis* can improve repetitive behavior in subjects having adult gut microbiomes and exhibiting ASD symptoms in accordance with some embodiments described herein.

Example 3: Adult Treatment Demonstrating Treatment of Adult MIA Mice (having a Characteristic Adult Microbiome) with a Probiotic Comprising *B. fragilis* Increases Communication Behavior in Accordance with Some Embodiments Described Herein 6-week-old offspring of immune-activated mothers were given applesauce containing *B. fragilis* or applesauce alone for 1 week. 4 weeks after bacterial treatment, male mice were tested for communicative behavior, as measured by production of ultrasonic vocalization in response to exposure to unfamiliar female mice. Adult treatment with *B. fragilis* increased number of calls produced by MIA offspring as compared to untreated controls (see FIG. 3). Poly(I:C) was administered as an immune activator in mothers. Offspring of non-immune activated mothers (saline treatment) were examined as additional controls. Abbreviations used in FIG. 3: Sal=saline offspring controls, pIC=poly (I:C) offspring, NB=sodium bicarbonate vehicle, BF=*B. fragilis*.

Communication behavior, as measured by production of ultrasonic vocalization was increased in the *B. fragilis*-treated adult offspring of immune-activated mothers than in untreated controls. Accordingly, treatment with a probiotic comprising, consisting essentially of, or consisting of *B. fragilis* can improve communication behavior in subjects having adult gut microbiomes and exhibiting ASD symptoms in accordance with some embodiments described herein.

Example 4: Correction of ASD-Relevant Behaviors by *B. fragilis*

A human subject exhibits anxiety and impaired sociability. The subject is determined to have a gut microbiotic profile comprising at least 800 different microbial species via high-throughput sequencing (and alignment) of nucleic acids isolated from a fecal sample of the subject. The subject consumes a gel capsule comprising an effective amount of a probiotic consisting essentially of *B. fragilis* weekly for eight weeks. After about eight weeks of consuming the gel capsule, the subject is expected to exhibit improved anxiety and sociability.

Example 5: Correction of ASD-Relevant Behaviors by *B. fragilis*

A human subject exhibits repetitive behavior and impaired language comprehension and usage. The subject is determined to have a gut microbiotic profile comprising at least 1000 different microbial species via high-throughput sequencing (and alignment) of nucleic acids isolated from a fecal sample of the subject. The subject consumes a cereal bar comprising an effective amount of a probiotic consisting essentially of *B. fragilis* until the symptoms are expected to improve. The subject is expected to exhibit improved repetitive behavior and impaired language comprehension and usage.

Example 5: Correction of ASD-Relevant Behaviors by *B. thetaiotaomicron*

A human subject exhibits repetitive behavior and impaired language comprehension and usage. The subject is determined to have a gut microbiotic profile comprising at least 1000 different microbial species via high-throughput sequencing (and alignment) of nucleic acids isolated from a fecal sample of the subject, including relative quantities (from greatest to least) of the following phyla: Firmicutes>Bacteroidetes>Actinobacteria>Proteobacteria. The subject consumes a yogurt drink comprising an effective amount of a probiotic consisting essentially of *B. thetaiotaomicron* until the symptoms are expected to improve. The yogurt drink is substantially free of drugs and antibiotics. The subject is expected to exhibit improved repetitive behavior and impaired language comprehension and usage.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

What is claimed is:

1. A method for improving behavioral performance in a human subject, the method comprising:
    identifying a human subject who is at least 20 years old, having:
        anxiety, autism spectrum disorder (ASD), or schizophrenia; and
        an adult gut microbiota signature, said adult gut microbiota signature comprising at least 500 different species of microbes,
    as a human subject in need of improving behavioral performance; and
    administering to the human subject in need of improving behavioral performance an effective amount of one or more *Bacteroides* bacteria, thereby improving behavioral performance in the human subject.

2. The method of claim 1, wherein the subject suffers from ASD.

3. The method of claim 1, wherein the effective amount of one or more *Bacteroides* bacteria comprises *B. fragilis*.

4. The method of claim 1, wherein the effective amount of one or more *Bacteroides* bacteria comprises *B. fragilis, B. thetaiotaomicron, B. vulgatus*, or a mixture of two or three of the listed bacteria.

5. The method of claim 1, further comprising administering an amount of *Enterococcus* bacteria to the human subject.

6. The method of claim 1, wherein said administering consists essentially of administering the effective amount of the one or more *Bacteroides* bacteria.

7. The method of claim 6, wherein the one or more *Bacteroides* bacteria is *B. fragilis*.

8. The method of claim 1, wherein the effective amount of one or more *Bacteroides* bacteria is in a composition substantially free of bacteria other than the *Bacteroides* bacteria.

9. The method of claim 1, wherein the effective amount of one or more *Bacteroides* bacteria is in a composition substantially free of bacteria other than *B. fragilis*.

10. The method of claim 1, wherein the effective amount of one or more *Bacteroides* bacteria is administered orally.

11. The method of claim 1, wherein improving behavioral performance comprises improving a communication behavior, a repetitive behavior, anxiety, or a combination of two or three of these listed behaviors.

12. The method of claim 1, wherein the effective amount of the one or more *Bacteroides* bacteria is administered in a single composition.

13. The method of claim 1, wherein the effective amount of the one or more *Bacteroides* bacteria is administered in two or more compositions.

14. The method of claim 5, wherein the *Enterococcus* bacteria is selected from the group consisting of: *E. faecilis, E. faecium, E. hirae, E. avium, E. durans, E. gallinarum*, and *E. casseliflavus*.

15. The method of claim 1, wherein the gut microbiota signature comprises at least 1000 different species of microbes.

16. The method of claim 1, wherein the gut microbiota signature comprises at least 500 different species of microbes as determined by comparison of sequences of 16s rRNA subunits.

* * * * *

UNITED STATES PATENT AND TRADEMARK OFFICE
CERTIFICATE OF CORRECTION

PATENT NO. : 10,111,914 B2
APPLICATION NO. : 14/925510
DATED : October 30, 2018
INVENTOR(S) : Antoinette Bailey It is certified that error appears in the above-identified patent and that said Letters Patent is hereby corrected as shown below:

On the Title Page

Item (57), Line 7, change "*thetaiomtaomicron,*" to --*thetaiotaomicron,*--.

Item (56), page 3, Line 24, under Other Publications, change "Heljtz," to --Heijtz,--.

Item (56), page 4, Line 26, under Other Publications, change "Napolionl," to --Napolioni,--.

In the Specification

Column 1, Line 48, change "microbiotia" to --microbiota--.

Column 2, Line 6, change "*Bacteroidies*" to --*Bacteroides*--.

Column 6, Line 35, change ""neutraceutical"" to --"nutraceutical"--.

Column 8, Line 12, change "*E. faecilis*" to --*E. faecalis*--.

Column 8, Line 18, change "*E. faecilis*" to --*E. faecalis*--.

Column 8, Line 20, change "*E. faecilis*" to --*E. faecalis*--.

Column 8, Line 23, change "*E. faecilis*" to --*E. faecalis*--.

Column 8, Lines 25-26, change "*E. faecilis*" to --*E. faecalis*--.

Column 8, Line 28, change "*E. faecilis*" to --*E. faecalis*--.

Column 8, Line 31, change "*E. faecilis*" to --*E. faecalis*--.

Signed and Sealed this
Second Day of April, 2019

Andrei Iancu
*Director of the United States Patent and Trademark Office*

Column 8, Line 34, change "*E. faecilis*" to --*E. faecalis*--.

Column 8, Lines 35-36, change "*E. faecilis*" to --*E. faecalis*--.

Column 8, Line 37, change "*E. faecilis*" to --*E. faecalis*--.

Column 8, Line 38, change each of the first and second instance of "*E. faecilis*" to --*E. faecalis*--.

Column 8, Line 39, change "*E. faecilis*" to --*E. faecalis*--.

Column 8, Lines 40-41, change "*E. faecilis*" to --*E. faecalis*--.

Column 9, Line 33, change "*E. faecilis*" to --*E. faecalis*--.

Column 9, Line 39, change "*E. faecilis*" to --*E. faecalis*--.

Column 9, Line 42, change "*E. faecilis*" to --*E. faecalis*--.

Column 9, Line 44, change "*E. faecilis*" to --*E. faecalis*--.

Column 9, Line 47, change "*E. faecilis*" to --*E. faecalis*--.

Column 9, Line 49, change "*E. faecilis*" to --*E. faecalis*--.

Column 9, Line 55, change "*E. faecilis*" to --*E. faecalis*--.

Column 9, Line 57, change "*E. faecilis*" to --*E. faecalis*--.

Column 10, Line 61, change "*casseliflavum*);" to --*casseliflavus*);--.

Column 23, Line 50, change "colosum," to --callosum,--.

In the Claims

Column 30, Line 33, Claim 14, change "*E. faecilis*" to --*E. faecalis*--.